US007964717B2

(12) United States Patent
Gleave et al.

(10) Patent No.: US 7,964,717 B2
(45) Date of Patent: Jun. 21, 2011

(54) RNAI PROBES TARGETING CANCER-RELATED PROTEINS

(75) Inventors: Martin E. Gleave, Vancouver (CA); Burkhard Jansen, Vancouver (CA); Ioannis P. Trougakos, Athens (GR); Efstathios Gonos, Athens (GR); Maxim Signaevsky, Vancouver (CA); Eliana Beraldi, Vancouver (CA)

(73) Assignee: The University of British Columbia, Vancouver (CA)

( * ) Notice: Subject to any disclaimer, the term of this patent is extended or adjusted under 35 U.S.C. 154(b) by 340 days.

(21) Appl. No.: 11/276,300

(22) Filed: Feb. 23, 2006

(65) Prior Publication Data

US 2006/0178329 A1     Aug. 10, 2006

Related U.S. Application Data

(62) Division of application No. 10/646,436, filed on Aug. 21, 2003.

(60) Provisional application No. 60/405,193, filed on Aug. 21, 2002, provisional application No. 60/408,152, filed on Sep. 3, 2002, provisional application No. 60/472,387, filed on May 20, 2003.

(51) Int. Cl.
*C07H 21/04* (2006.01)

(52) U.S. Cl. ............ 536/24.5; 536/24.1; 536/24.31; 435/6; 435/325; 435/375; 514/44

(58) Field of Classification Search .................. None
See application file for complete search history.

(56) References Cited

U.S. PATENT DOCUMENTS

| | | | |
|---|---|---|---|
| 6,140,126 A * | 10/2000 | Bennett et al. | ............ 435/375 |
| 6,284,741 B1 * | 9/2001 | Werther et al. | ............ 514/44 |
| 2002/0086356 A1 | 7/2002 | Tuschl et al. | |
| 2003/0158130 A1 | 8/2003 | Gleave et al. | |
| 2004/0259247 A1 * | 12/2004 | Tuschl et al. | ............ 435/375 |
| 2006/0003322 A1 * | 1/2006 | Bentwich | ............ 435/6 |

FOREIGN PATENT DOCUMENTS

| WO | WO 00/49937 A2 | 6/2000 |
|---|---|---|
| WO | WO 00/69454 | 11/2000 |
| WO | WO 01/05435 A2 | 1/2001 |
| WO | WO 01/75164 A2 | 10/2001 |
| WO | WO 02/22635 A1 | 3/2002 |
| WO | WO 02/22642 A1 | 3/2002 |
| WO | WO 02/44321 A2 | 6/2002 |
| WO | WO 03/062421 A1 | 7/2003 |

OTHER PUBLICATIONS

Zangemeister et al. A Novel Bispecific Antisense Oligonucleotide Inhibiting Both bcl-2 and bcl-xl Expression Efficiently Induces Apoptosis in Tuymor Cell. Clinical Cancer Research, 2000, vol. 6: 2547-2555.*

Zhang et al. Targeted Gene Silencing by Small Interfering RNA based Knock-down TEchnology. Current Pharmaceutical Biotechnology 2004, vol. 5, p. 1-7.*

Mahato et al. Modulation of gene expression by antisense and antigene oligodeoxynucleotides and small interfering RNA. Expert Opin. Deliv. 2005, vol. 2(1): 3-28.*

Scherer et al. Approaches for the Sequence-specific knockdown of mRNA (Nat. Biotechnol., 2003, 21(12), pp. 1457-1465).*

Leirdal et al. Gene silencing in mammalian cells by preformed small RNA duplexes. Biochem and Biophys Res Comm 295 (2002) 744-748.*

Agami, RNAi and related mechanisms and their potential use for therapy, Current Opinion in Chemical Biology, 2002, pp. 829-834, vol. 6, Publisher: Current Biology Ltd, London, GB XP00295888.

Brummelkamp et al., A system for stable expression of short interfering RNAs in mammalian cells, Science, 2002, pp. 550-553, vol. 296, No. 5567, Publisher: American Association for the Advancement of Science, US, XP002234902.

Calero et al., Apolipoprotein J (Clusterin) and Alzheimer's Disease, Microscopy Research and Technique, 2000, pp. 305-315, vol. 50, No. 4, XP009021345.

Choi-Miura et al., Relationship Between Multifunctional Protein "Clusterin" and Alzheimer Disease, Neurobiology of Aging, 1996, pp. 717-722, vol. 17, No. 5, XP001146408.

Demir et al., Use of RNA Interference (RNAi) to Disrupt C-Kit Gene Expression in Malignant Human Hematopoietic and Neuroepithelial Cells, Blood, 2000, p. 378B, vol. 96, No. 11, Part 2, Publisher: W. B. Saunders Company, Orlando, FL, US, Abstract #5389, XP009004894.

Gleave et al., Use of Antisense Oligonucleotides Targeting the Antiapoptotic Gene, Clusterin/Testosterone-Repressed Prostate Message 2, to Enhance Androgen Sensitivity and Chemosensitivity in Prostate Cancer, Urology, 2001, pp. 39-49, vol. 58, XP002262320.

Gleave et al., Targeting anti-apoptotic genes upregulated by androgen withdrawal using antisense oligonucleotides to enhance androgen- and chemo-sensitivity in prostate cancer, Investigational New Drugs, 2002, pp. 145-158, vol. 20, No. 2, XP 009021411.

Hojoh, RNA interference (RNAi) induction with various types of synthetic oligonucleotide duplexes in cultered human cells, FEBS Letters, 2002, pp. 195-199, vol. 521, No. 1-3, Publisher: Elsevier Science Publishers, Amsterdam, NL XP004362164.

(Continued)

*Primary Examiner* — Kimberly Chong
(74) *Attorney, Agent, or Firm* — Larson & Anderson, LLC

(57) ABSTRACT

RNAi sequences that are useful as therapeutics in the treatment of cancers of various types, including prostate cancer, sarcomas such as osteosarcoma, renal cell carcinoma, breast cancer, bladder cancer, lung cancer, colon cancer, ovarian cancer, anaplastic large cell lymphoma and melanoma; and Alzheimer's disease. These sequences target clusterin, IGFBP-5, IGFBP-2, both IGFBP-2 and -5 simultaneously, Mitf, and B-raf. The invention further provides for the use of these RNAi sequences in the treatment of cancers of various types, including prostate cancer, sarcomas such as osteosarcoma, renal cell carcinoma, breast cancer, bladder cancer, lung cancer, colon cancer, ovarian cancer, anaplastic large cell lymphoma and melanoma; and Alzheimer's disease, and a method of treating such conditions through the administration of the RNA molecules with RNAi activity to an individual, including a human individual in need of such treatment.

21 Claims, 17 Drawing Sheets

OTHER PUBLICATIONS

Jones et al., Molecules in focus: Clusterin, The International Journal of Biochemistry & Cell Biology, 2002, pp. 427-431, vol. 34, XP002262319.

Koch-Brandt et al., Clusterin: A Role in Cell Survival in the Face of Apoptosis?, Process in Molecular and Subcellar Biology, 1996, pp. 130-149, vol. 16, XP009021385.

Miyake et al., Antisense TRPM-2 Oligodeoxynucleotides Chemosensitize Human Androgen-independent PC-3 Prostate Cancer Cells Both in Vitro and in Vivo, Clinical Cancer Research, 2000, pp. 1655-1663, vol. 6, No. 5, Publisher: The American Association for Cancer Research, US, XP000960694.

Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity., International Journal of Urology, 2001, pp. 337-349, vol. 8, No. 7, XP002262321.

Paddison et al., Stable suppression of gene expression by RNAi in mammalian cells, Proceedings of the National Academy of Sciences of USA, 2002, pp. 1443-1448, vol. 99, No. 3, Publisher: National Academy of Science, XP002958887.

Rosenberg et al., Clusterin: Physiologic and Pathophysiologic Considerations, Int. J. Biochem. Cell Biol., 1995, pp. 633-645, vol. 27, No. 7, XP001002844.

Sensibar et al., Prevention of Cell Death Induced by Tumor Necrosis Factor α in LNCaP Cells by Overexpression of Sulfated Glycoprotein-2 (Clusterin), Cancer Research, 1995, pp. 2431-2437, vol. 55, Publisher: American Association for Cancer Research, Baltimore, MD, US, XP002930082.

Sharp, RNAi and double-strand RNA, Genes and Development, 1999, pp. 139-141, vol. 13, No. 2, Publisher: Cold Spring Harbor Laboratory Press, New York, US, XP002171268.

Strocchi et al., Neuronal loss up-regulates clusterin mRNA in living neurons and glial cells in the rat brain, NeuroReport, 1999, pp. 1789-1792, vol. 10, No. 8, Publisher: Rapid Communications of Oxford, Oxford, GB, XP009017327.

Sui et al., A DNA vector-based RNAi technology to suppress gene expression in mammalian cells, Proceddings of the National Academy of Sciences of USA, 2002, pp. 5515-5520, vol. 99, No. 8, Publisher: National Academy of Science, Washington, US, XP002964701.

Tuschl et al., Targeted mRNA degradation by double-stranded RNA in vitro, Genes and Development, 1999, pp. 3191-3197, vol. 13, No. 24, Publisher: Cold Spring Harbor Laboratory Press, New York, US, XP002183118.

Ueda, RNAi: A new technology in the post-genomic sequencing era, Journal of Neurogenetics, 2001, pp. 193-204, vol. 15, No. 3/4, Publisher: Elsevier, Amsterdam, NL, XP001147227.

Wilson et al., Clusterin is a secreted mammalian chaperone, Trends in Biochemical Sciences, 2000, pp. 95-98, vol. 25, No. 3, Publisher: Elsevier Publication, Cambridge, EN, XP004202536.

Wong et al., Molecular characterization of human TRPM-2/clusterin, a gene associated with sperm maturation, apoptosis and neurodegeneration, European Journal of Biochemistry,1994, pp. 917-925, vol. 227, No. 3, XP 001146404.

Zellweger et al., Antitumor Activity of Antisense Clusterin Oligonucleotides is Improved in Vitro and in Vivo by Incorporation of 2'O-(2-Methoxy)Ethyl Chemistry, Journal of Pharmacology and Expermental Therapeutics, 2001, pp. 934-940, vol. 298, No. 3, XP002262318.

Chako et al., Double-stranded ribonucleic acid decreases C6 rat glioma cell numbers: Effects on insulin-like growth factor I gene expression and action, Endocrinology, Oct. 2000, vol. 141, No. 10, pp. 3546-3555.

Pavelic et al., Insulin-like growth factor family and combined antisense approach in therapy of lung carcinoma, Molecular Medicine, Mar. 2002, vol. 8, No. 3, pp. 149-157.

Miyake, et al., Castration-Induced Up-Regulation of Insulin-Like Growth Factor Binding Protein-5 Potentiates Insulin-Like Growth Factor-I Activity and Accelerates Progression to Androgen Independence in Prostate Cancer Models, Cancer Research, Jun. 1, 2000, pp. 3058-3064, vol. 60.

Davies et al., Mutations of the BRAF gene in human cancer, Nature, , pp. 949-954, vol. 417, 2002.

Gewirtz, A Critical Evaluation of the Mechanisms of Action Proposed for the Antitumor Effects of the Anthracycline Antibiotics , Biochemical Pharmacology, , pp. 727-741, vol. 57, 1999.

Harborth et al., Identification of essential genes in cultured mammalian cells using small interfering RNAs, Journal of Cell Science, , pp. 4557-4565, vol. 114, 2001.

Leskov et al., Synthesis and Functional Analyses of Nuclear Clusterin, a Cell Death Protein, The Journal of Biological Chemistry, , pp. 11590-11600, vol. 278, No. 13, 2003.

McGill et al., Bcl2 Regulation by the Melanocyte Master Regulator Mitf Modulates Lineage Survival and Melanoma Cell Viability, Cell, , pp. 707-718, vol. 109, 2002.

Muller et al., Cellular pharmacokinetics of doxorubicin in patients with chronic lymphocytic leukemia: comparision of bolus administr . . . , Cancer Chemother Pharmacol, , pp. 379-384, vol. 32, 1993.

Rohlff et al., Prostate Cancer Cell Growth Inhibition by Tamoxifen is Associated With Inhibition of Protein Kinase C and Induction of . . . , The Prostate, , pp. 51-59, vol. 37, 1998.

Carthew, Gene silencing by double-stranded RNA, Current Opinion in Cell Biology, 2001, pp. 244-248, vol. 13.

Demattos et al., Clusterin promotes amyloid plaque formation and is critical for neuritic toxicity in a mouse model of Alzheimer's disease, PNAS, 2002, pp. 10843-10848, vol. 99, No. 16.

Elbashir et al., Duplexes of 21-nucleotide RNAs mediate RNA interference in cultured mammalian cells, Nature, 2001, pp. 494-498, vol. 411.

Fire et al., Potent and specific genetic interference by double-stranded RNA in *Caenorhabditis elegans*, Nature,1998, pp. 806-811, vol. 391.

Yang et al., Nuclear clusterin/XIP8, an x-ray-induced Ku70-binding protein that signals cell death, PNAS, 2000, pp. 5907-5912, vol. 97, No. 11.

\* cited by examiner

Clusterin Levels From Western

SEQUENCE LISTING

```
<160> NUMBER OF SEQ ID NOS: 68

<210> SEQ ID NO 1
<211> LENGTH: 21
<212> TYPE: DNA
<213> ORGANISM: artificial
<220> FEATURE:
<223> OTHER INFORMATION: RNAi for human clusterin

<400> SEQUENCE: 1
ccagagcucg cccuucuact t                                              21
```

-continued

<210> SEQ ID NO 2
<211> LENGTH: 21
<212> TYPE: DNA
<213> ORGANISM: artificial
<220> FEATURE:
<223> OTHER INFORMATION: RNAi for human clusterin

<400> SEQUENCE: 2
guagaagggc gagcucuggt t                                              21

<210> SEQ ID NO 3
<211> LENGTH: 21
<212> TYPE: DNA
<213> ORGANISM: artificial
<220> FEATURE:
<223> OTHER INFORMATION: RNAi for human clusterin

<400> SEQUENCE: 3
gaugcucaac accuccucct t                                              21

<210> SEQ ID NO 4
<211> LENGTH: 21
<212> TYPE: DNA
<213> ORGANISM: artificial
<220> FEATURE:
<223> OTHER INFORMATION: RNAi for human clusterin

<400> SEQUENCE: 4
ggaggaggug uugagcauct t                                              21

<210> SEQ ID NO 5
<211> LENGTH: 21
<212> TYPE: DNA
<213> ORGANISM: artificial
<220> FEATURE:
<223> OTHER INFORMATION: RNAi for human clusterin

<400> SEQUENCE: 5
cuaauucaau aaaacuguct t                                              21

<210> SEQ ID NO 6
<211> LENGTH: 21
<212> TYPE: DNA
<213> ORGANISM: artificial
<220> FEATURE:
<223> OTHER INFORMATION: RNAi for human clusterin

<400> SEQUENCE: 6
gacaguuuua uugaauuagt t                                              21

<210> SEQ ID NO 7
<211> LENGTH: 19
<212> TYPE: DNA
<213> ORGANISM: artificial
<220> FEATURE:
<223> OTHER INFORMATION: RNAi for human clusterin

<400> SEQUENCE: 7
uaauucaaca aaacugutt                                                 19

<210> SEQ ID NO 8
<211> LENGTH: 19
<212> TYPE: DNA
<213> ORGANISM: artificial
<220> FEATURE:
<223> OTHER INFORMATION: RNAi for human clusterin

<400> SEQUENCE: 8
acaguuuugu ugaauuatt                                           19

<210> SEQ ID NO 9
<211> LENGTH: 21
<212> TYPE: DNA
<213> ORGANISM: artificial
<220> FEATURE:
<223> OTHER INFORMATION: RNAi for human clusterin

<400> SEQUENCE: 9
augaugaaga cucugcugct t                                        21

<210> SEQ ID NO 10
<211> LENGTH: 21
<212> TYPE: DNA
<213> ORGANISM: artificial
<220> FEATURE:
<223> OTHER INFORMATION: RNAi for human clusterin

<400> SEQUENCE: 10
gcagcagagu cuucaucaut t                                        21

<210> SEQ ID NO 11
<211> LENGTH: 22
<212> TYPE: DNA
<213> ORGANISM: artificial
<220> FEATURE:
<223> OTHER INFORMATION: RNAi for human clusterin

<400> SEQUENCE: 11
ugaaugaagg gacuaaccug tt                                       22

<210> SEQ ID NO 12
<211> LENGTH: 22
<212> TYPE: DNA
<213> ORGANISM: artificial
<220> FEATURE:
<223> OTHER INFORMATION: RNAi for human clusterin

<400> SEQUENCE: 12
cagguuaguc ccuucauuca tt                                       22

<210> SEQ ID NO 13
<211> LENGTH: 22
<212> TYPE: DNA
<213> ORGANISM: artificial
<220> FEATURE:
<223> OTHER INFORMATION: RNAi for human clusterin

<400> SEQUENCE: 13
cagaaauaga caaagugggg tt                                       22

<210> SEQ ID NO 14
<211> LENGTH: 22
<212> TYPE: DNA
<213> ORGANISM: artificial
<220> FEATURE:
<223> OTHER INFORMATION: RNAi for human clusterin

<400> SEQUENCE: 14
ccccacuuug ucuauuucug tt                                       22

```
<210> SEQ ID NO 15
<211> LENGTH: 22
<212> TYPE: DNA
<213> ORGANISM: artificial
<220> FEATURE:
<223> OTHER INFORMATION: RNAi for human clusterin

<400> SEQUENCE: 15
acagagacua agggaccaga tt                                              22

<210> SEQ ID NO 16
<211> LENGTH: 22
<212> TYPE: DNA
<213> ORGANISM: artificial
<220> FEATURE:
<223> OTHER INFORMATION: RNAi for human clusterin

<400> SEQUENCE: 16
acagagacua agggaccaga tt                                              22

<210> SEQ ID NO 17
<211> LENGTH: 20
<212> TYPE: DNA
<213> ORGANISM: artificial
<220> FEATURE:
<223> OTHER INFORMATION: RNAi for human IGFBP-5

<400> SEQUENCE: 17
augguguugc ucaccgcgtt                                                 20

<210> SEQ ID NO 18
<211> LENGTH: 20
<212> TYPE: DNA
<213> ORGANISM: artificial
<220> FEATURE:
<223> OTHER INFORMATION: RNAi for human IGFBP-5

<400> SEQUENCE: 18
cgcggugagc aacaccautt                                                 20

<210> SEQ ID NO 19
<211> LENGTH: 22
<212> TYPE: DNA
<213> ORGANISM: artificial
<220> FEATURE:
<223> OTHER INFORMATION: RNAi for human IGFBP-5

<400> SEQUENCE: 19
cccugggcug cgagcugguc tt                                              22

<210> SEQ ID NO 20
<211> LENGTH: 22
<212> TYPE: DNA
<213> ORGANISM: artificial
<220> FEATURE:
<223> OTHER INFORMATION: RNAi for human IGFBP-5

<400> SEQUENCE: 20
gaccagcucg cagcccaggg tt                                              22

<210> SEQ ID NO 21
<211> LENGTH: 22
<212> TYPE: DNA
<213> ORGANISM: artificial
<220> FEATURE:
<223> OTHER INFORMATION: RNAi for human IGFBP-5
```

```
<400> SEQUENCE: 21
gaggaaacug aggaccucgg tt                                              22

<210> SEQ ID NO 22
<211> LENGTH: 22
<212> TYPE: DNA
<213> ORGANISM: artificial
<220> FEATURE:
<223> OTHER INFORMATION: RNAi for human IGFBP-5

<400> SEQUENCE: 22
ccgagguccu caguuccuc tt                                               22

<210> SEQ ID NO 23
<211> LENGTH: 22
<212> TYPE: DNA
<213> ORGANISM: artificial
<220> FEATURE:
<223> OTHER INFORMATION: RNAi for human IGFBP-5

<400> SEQUENCE: 23
cucggauucu caugcaaggg tt                                              22

<210> SEQ ID NO 24
<211> LENGTH: 22
<212> TYPE: DNA
<213> ORGANISM: artificial
<220> FEATURE:
<223> OTHER INFORMATION: RNAi for hman IGFBP-5

<400> SEQUENCE: 24
cccuugcuag agauuccgag tt                                              22

<210> SEQ ID NO 25
<211> LENGTH: 21
<212> TYPE: DNA
<213> ORGANISM: artificial
<220> FEATURE:
<223> OTHER INFORMATION: RNAi for human IGFBP-5

<400> SEQUENCE: 25
agcccucucc augugcccct t                                               21

<210> SEQ ID NO 26
<211> LENGTH: 21
<212> TYPE: DNA
<213> ORGANISM: artificial
<220> FEATURE:
<223> OTHER INFORMATION: RNAi for human IGFBP-5

<400> SEQUENCE: 26
ggggcacaug gagagggcut t                                               21

<210> SEQ ID NO 27
<211> LENGTH: 21
<212> TYPE: DNA
<213> ORGANISM: artificial
<220> FEATURE:
<223> OTHER INFORMATION: RNAi for human IGFBP-5

<400> SEQUENCE: 27
gaagcugacc caguccaagt t                                               21
```

```
<210> SEQ ID NO 28
<211> LENGTH: 21
<212> TYPE: DNA
<213> ORGANISM: artificial
<220> FEATURE:
<223> OTHER INFORMATION: RNAi for human IGFBP-5

<400> SEQUENCE: 28
cuuggacugg gucagcuuct t                                              21

<210> SEQ ID NO 29
<211> LENGTH: 22
<212> TYPE: DNA
<213> ORGANISM: artificial
<220> FEATURE:
<223> OTHER INFORMATION: RNAi for human IGFBP-5

<400> SEQUENCE: 29
gcugccaggc auggaguacg tt                                             22

<210> SEQ ID NO 30
<211> LENGTH: 22
<212> TYPE: DNA
<213> ORGANISM: artificial
<220> FEATURE:
<223> OTHER INFORMATION: RNAi for human IGFBP-5

<400> SEQUENCE: 30
cguacuccau gccuggcagc tt                                             22

<210> SEQ ID NO 31
<211> LENGTH: 23
<212> TYPE: DNA
<213> ORGANISM: artificial
<220> FEATURE:
<223> OTHER INFORMATION: RNAi for human IGFBP-2

<400> SEQUENCE: 31
augcugccga gagugggcug ctt                                            23

<210> SEQ ID NO 32
<211> LENGTH: 23
<212> TYPE: DNA
<213> ORGANISM: artificial
<220> FEATURE:
<223> OTHER INFORMATION: RNAi for human IGFBP-2

<400> SEQUENCE: 32
gcagcccacu cucggcagca utt                                            23

<210> SEQ ID NO 33
<211> LENGTH: 21
<212> TYPE: DNA
<213> ORGANISM: artificial
<220> FEATURE:
<223> OTHER INFORMATION: RNAi for human IGFBP-2

<400> SEQUENCE: 33
ccccuguguc ccuuuugcat t                                              21

<210> SEQ ID NO 34
<211> LENGTH: 21
<212> TYPE: DNA
<213> ORGANISM: artificial
<220> FEATURE:
<223> OTHER INFORMATION: RNAi for human IGFBP-2
```

```
<400> SEQUENCE: 34
ugcaaaaggg acacaggggt t                                              21

<210> SEQ ID NO 35
<211> LENGTH: 21
<212> TYPE: DNA
<213> ORGANISM: artificial
<220> FEATURE:
<223> OTHER INFORMATION: RNAi for human IGFBP-2

<400> SEQUENCE: 35
cugugacaag cauggccugt t                                              21

<210> SEQ ID NO 36
<211> LENGTH: 21
<212> TYPE: DNA
<213> ORGANISM: artificial
<220> FEATURE:
<223> OTHER INFORMATION: RNAi for human IGFBP-2

<400> SEQUENCE: 36
caggccaugc uugucacagt t                                              21

<210> SEQ ID NO 37
<211> LENGTH: 20
<212> TYPE: DNA
<213> ORGANISM: artificial
<220> FEATURE:
<223> OTHER INFORMATION: RNAi for human IGFBP-2

<400> SEQUENCE: 37
gcgccgggac gccgaguatt                                                20

<210> SEQ ID NO 38
<211> LENGTH: 20
<212> TYPE: DNA
<213> ORGANISM: artificial
<220> FEATURE:
<223> OTHER INFORMATION: RNAi for human IGFBP-2

<400> SEQUENCE: 38
uacucggcgu cccggcgctt                                                20

<210> SEQ ID NO 39
<211> LENGTH: 21
<212> TYPE: DNA
<213> ORGANISM: artificial
<220> FEATURE:
<223> OTHER INFORMATION: RNAi for humanIGFBP-2 and -5

<400> SEQUENCE: 39
ggagccgggc ugcggcugct t                                              21

<210> SEQ ID NO 40
<211> LENGTH: 21
<212> TYPE: DNA
<213> ORGANISM: artificial
<220> FEATURE:
<223> OTHER INFORMATION: RNAi for human IGFBP-2 and -5

<400> SEQUENCE: 40
gcagccgcag cccggcucct t                                              21
```

```
<210> SEQ ID NO 41
<211> LENGTH: 19
<212> TYPE: DNA
<213> ORGANISM: artificial
<220> FEATURE:
<223> OTHER INFORMATION: RNAi for human IGFBP-2 and -5

<400> SEQUENCE: 41
cgugcggcgu cuacacctt                                                19

<210> SEQ ID NO 42
<211> LENGTH: 19
<212> TYPE: DNA
<213> ORGANISM: artificial
<220> FEATURE:
<223> OTHER INFORMATION: RNAi for human IGFBP-2 and -5

<400> SEQUENCE: 42
gguguagacg ccgcacgtt                                                19

<210> SEQ ID NO 43
<211> LENGTH: 18
<212> TYPE: DNA
<213> ORGANISM: artificial
<220> FEATURE:
<223> OTHER INFORMATION: RNAi for human IGFBP-2 and -5

<400> SEQUENCE: 43
ccaggggcug cgcugctt                                                 18

<210> SEQ ID NO 44
<211> LENGTH: 18
<212> TYPE: DNA
<213> ORGANISM: artificial
<220> FEATURE:
<223> OTHER INFORMATION: RNAi for human IGFBP-2 and -5

<400> SEQUENCE: 44
gcagcgcagc cccuggtt                                                 18

<210> SEQ ID NO 45
<211> LENGTH: 22
<212> TYPE: DNA
<213> ORGANISM: artificial
<220> FEATURE:
<223> OTHER INFORMATION: RNAi for human Mitf

<400> SEQUENCE: 45
ccgcugaaga gcagcaguud tt                                            22

<210> SEQ ID NO 46
<211> LENGTH: 21
<212> TYPE: DNA
<213> ORGANISM: artificial
<220> FEATURE:
<223> OTHER INFORMATION: RNAi for human Mitf

<400> SEQUENCE: 46
aacugcugcu cuucagcggt t                                             21

<210> SEQ ID NO 47
<211> LENGTH: 21
<212> TYPE: DNA
<213> ORGANISM: artificial
<220> FEATURE:
<223> OTHER INFORMATION: RNAi for human Mitf
```

<400> SEQUENCE: 47
augcaggcuc gagcucaugt t                                    21

<210> SEQ ID NO 48
<211> LENGTH: 21
<212> TYPE: DNA
<213> ORGANISM: artificial
<220> FEATURE:
<223> OTHER INFORMATION: RNAi for human Mitf

<400> SEQUENCE: 48
caugagcucg agccugcaut t                                    21

<210> SEQ ID NO 49
<211> LENGTH: 21
<212> TYPE: DNA
<213> ORGANISM: artificial
<220> FEATURE:
<223> OTHER INFORMATION: RNAi for human Mitf

<400> SEQUENCE: 49
agauacagua ccccucuagt t                                    21

<210> SEQ ID NO 50
<211> LENGTH: 21
<212> TYPE: DNA
<213> ORGANISM: artificial
<220> FEATURE:
<223> OTHER INFORMATION: RNAi for human Mitf

<400> SEQUENCE: 50
cuagaggggu acuguaucut t                                    21

<210> SEQ ID NO 51
<211> LENGTH: 21
<212> TYPE: DNA
<213> ORGANISM: artificial
<220> FEATURE:
<223> OTHER INFORMATION: RNAi for human b-raf

<400> SEQUENCE: 51
ucucuggggu ucgguucugt t                                    21

<210> SEQ ID NO 52
<211> LENGTH: 21
<212> TYPE: DNA
<213> ORGANISM: artificial
<220> FEATURE:
<223> OTHER INFORMATION: RNAi for human b-raf

<400> SEQUENCE: 52
caguuccguu ccccagagat t                                    21

<210> SEQ ID NO 53
<211> LENGTH: 21
<212> TYPE: DNA
<213> ORGANISM: artificial
<220> FEATURE:
<223> OTHER INFORMATION: RNAi for human b-raf

<400> SEQUENCE: 53 ccugcaaua uugaugacut t                                     21

<210> SEQ ID NO 54
<211> LENGTH: 21
<212> TYPE: DNA
<213> ORGANISM: artificial
<220> FEATURE:
<223> OTHER INFORMATION: RNAi for human b-raf

<400> SEQUENCE: 54
agucaucaau auugacaggt t                                              21

<210> SEQ ID NO 55
<211> LENGTH: 21
<212> TYPE: DNA
<213> ORGANISM: artificial
<220> FEATURE:
<223> OTHER INFORMATION: RNAi for human b-raf

<400> SEQUENCE: 55
cccuccuugu uucgggcugt t                                              21

<210> SEQ ID NO 56
<211> LENGTH: 21
<212> TYPE: DNA
<213> ORGANISM: artificial
<220> FEATURE:
<223> OTHER INFORMATION: RNAi for human b-raf

<400> SEQUENCE: 56
cagcccgauu caaggagggt t                                              21

<210> SEQ ID NO 57
<211> LENGTH: 23
<212> TYPE: DNA
<213> ORGANISM: human

<400> SEQUENCE: 57
aaccagagct cgcccttcta ctt                                            23

<210> SEQ ID NO 58
<211> LENGTH: 21
<212> TYPE: DNA
<213> ORGANISM: artificial
<220> FEATURE:
<223> OTHER INFORMATION: RNAi for human clusterin

<400> SEQUENCE: 58
ccagagcucg cccuucuact t                                              21

<210> SEQ ID NO 59
<211> LENGTH: 21
<212> TYPE: DNA
<213> ORGANISM: artificial
<220> FEATURE:
<223> OTHER INFORMATION: RNAi for human clusterin

<400> SEQUENCE: 59
guagaagggc gagcucuggt t                                              21

<210> SEQ ID NO 60
<211> LENGTH: 23
<212> TYPE: DNA
<213> ORGANISM: human

<400> SEQUENCE: 60
aagtcccgca tcgtccgcag ctt                                            23

```
<210> SEQ ID NO 61
<211> LENGTH: 21
<212> TYPE: DNA
<213> ORGANISM: artificial
<220> FEATURE:
<223> OTHER INFORMATION: RNAi for human clusterin

<400> SEQUENCE: 61
gucccgcauc guccgcagct t                                              21

<210> SEQ ID NO 62
<211> LENGTH: 21
<212> TYPE: DNA
<213> ORGANISM: artificial
<220> FEATURE:
<223> OTHER INFORMATION: RNAi for human clusterin

<400> SEQUENCE: 62
gcugcggacg augcgggact t                                              21

<210> SEQ ID NO 63
<211> LENGTH: 23
<212> TYPE: DNA
<213> ORGANISM: human

<400> SEQUENCE: 63
aactaattca ataaaactgt ctt                                            23

<210> SEQ ID NO 64
<211> LENGTH: 21
<212> TYPE: DNA
<213> ORGANISM: artificial
<220> FEATURE:
<223> OTHER INFORMATION: RNAi for human clusterin

<400> SEQUENCE: 64
cuaauucaau aaaacuguct t                                              21

<210> SEQ ID NO 65
<211> LENGTH: 21
<212> TYPE: DNA
<213> ORGANISM: artificial
<220> FEATURE:
<223> OTHER INFORMATION: RNAi forhuman clusterin

<400> SEQUENCE: 65
gacaguuuua uugaauuagt t                                              21

<210> SEQ ID NO 66
<211> LENGTH: 23
<212> TYPE: DNA
<213> ORGANISM: human

<400> SEQUENCE: 66
gcatgatgaa gactctgctg ctg                                            23

<210> SEQ ID NO 67
<211> LENGTH: 19
<212> TYPE: RNA
<213> ORGANISM: artificial
<220> FEATURE:
<223> OTHER INFORMATION: RNAi for human clusterin

<400> SEQUENCE: 67
augaugaaga cucugcugc                                                 19
```

```
<210> SEQ ID NO 68
<211> LENGTH: 19
<212> TYPE: RNA
<213> ORGANISM: artificial
<220> FEATURE:
<223> OTHER INFORMATION: RNAi fo rhuman clusterin

<400> SEQUENCE: 68
gcagcagagu cuucaucau                                              19
```

RNAI PROBES TARGETING CANCER-RELATED PROTEINS

This application claims the benefit and priority of U.S. Provisional Applications Nos. 60/405,193, filed Aug. 21, 2002, 60/408,152 filed Sep. 3, 2002, and 60/472,387, filed May 20, 2003, all of which are incorporated herein by reference.

BACKGROUND OF THE INVENTION

This application relates to short double stranded RNAi probes useful in cancer therapy and treatment of other diseases. RNA interference or "RNAi" is a term initially coined by fire and co-workers to describe the observation that double-stranded RNA (dsRNA) can block gene expression when it is introduced into worms (Fire et al. (1998) Nature 391, 806-811, incorporated herein by reference). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The use of RNAi has been further described in Carthew et al. (2001) Current Opinions in Cell Biology 13, 244-248, and Elbashir et al. (2001) Nature 411, 494-498, both of which are incorporated herein by reference.

Within any given mRNA molecule, there are sites which are affected by RNAi probes, and sites which are not. Thus, one cannot simply chop up the overall sequence into subsequences of appropriate lengths (for example, 21 to 23 base pairs) to arrive at functional RNAi-based therapeutics. Indeed, published U.S. Pat. application Ser. No. 2002-0086356-A1 discloses a method for use in assessing where target sites might be located in a mRNA sequence, although this method is not the only approach to development of effective RNAi sequences.

SUMMARY OF THE INVENTION

The present invention provides RNAi sequences that are useful as therapeutics in the treatment of cancers of various types, including prostate cancer, sarcomas such as osteosarcoma, renal cell carcinoma, breast cancer, bladder cancer, lung cancer, colon cancer, ovarian cancer, anaplastic large cell lymphoma and melanoma; and Alzheimer's disease. These sequences target clusterin, IGFBP-5, IGFBP-2, both IGFBP-2 and -5 simultaneously, Mitf, and B-raf.

The invention further provides for the use of these RNAi sequences in the treatment of cancers of various types, including prostate cancer, sarcomas such as osteosarcoma, renal cell carcinoma, breast cancer, bladder cancer, lung cancer, colon cancer, ovarian cancer, anaplastic large cell lymphoma and melanoma; and Alzheimer's disease, and a method of treating such conditions through the administration of the RNA molecules with RNAi activity to an individual, including a human individual in need of such treatment.

BRIEF DESCRIPTION OF THE DRAWINGS

FIG. 8 shows the reduction in clusterin transcript as a result of treatment of A549 cells with clusterin-targeted siRNA as determined by RT-PCR.

DETAILED DESCRIPTION OF THE INVENTION

Figure 1A:
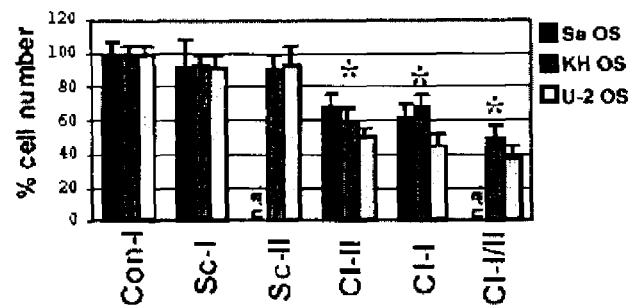
FIG. 1A shows relative growth rate, estimated by cell number counting of Sa OS, KH OS and U-2 OS cells following siRNA-mediated clusterin gene expression silencing. $5\times10^3$ cells/cell line were seeded in 6 well plates and after siRNA treatment for 70 hours the total number of cells was counted. A significant reduction in the cell number, that is more pronounced in U-2 OS cells was observed in all clusterin knockdown cells.

The present invention relates to isolated RNA molecules which mediate RNAi. That is, the isolated RNA molecules of the present invention mediate degradation of mRNA that is the transcriptional product of the gene, which is also referred to as a target gene. For convenience, such mRNA may also be referred to herein as mRNA to be degraded. The terms RNA, RNA molecule(s), RNA segment(s) and RNA fragment(s) may be used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAi compounds are referred to as analogs or analogs of naturally-occurring RNA. RNA of the present invention need only be sufficiently similar to natural RNA that it has the ability to mediate RNAi. As used herein the phrase "mediate RNAi" refers to and indicates the ability to distinguish which mRNA are to be affected by the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or lack of expression of the target mRNA.

As noted above, the RNA molecules of the present invention in general comprise an RNA portion and some additional portion, for example a deoxyribonucleotide portion. The total number of nucleotides in the RNA molecule is suitably less than 49 in order to be effective mediators of RNAi. In preferred RNA molecules, the number of nucleotides is 16 to 29, more preferably 18 to 23, and most preferably 21-23.

A first group of RNA molecules in accordance with the present invention are directed to mRNA encoding clusterin, a protein also known as testosterone-repressed prostate message-2 (TRPM-2) or sulfated glycoprotein-2 (SGP-2). Clusterin is expressed in increased amounts by prostate tumor cells following androgen withdrawal. Furthermore, it has been determined that antisense therapy which reduces the expression of clusterin provides therapeutic benefits in the treatment of cancer. In particular, such antisense therapy can be applied in treatment of prostate cancer and renal cell cancer. (PCT Patent Publication WO 00/49937, which is incorporated herein by reference). Administration of therapeutic agents clusterin also can enhance sensitivity of cancer cells to chemotherapeutic agents and to radiotherapy both in vitro and in vivo. Sequences of specific RNA molecules which may be used to interfere with the expression of clusterin are listed in Table 1 and 7. (See, US Pat. application Ser. No. 09/967,726 which is incorporated herein by reference) These sequences can be used alone or in combination with other chemotherapy agents or apoptosis inducing treatment concepts in the treatment of prostate cancer, sarcomas such as osteosarcoma, renal cell carcinoma, breast cancer, bladder cancer, lung cancer, colon cancer, ovarian cancer, anaplastic large cell lymphoma and melanoma. In addition, clusterin has been shown to promote amyloid plaque formation and to be critical for neuritic toxicity in mouse models for Alzheimer's disease. (De Mattos et al., Proc. Nat'l Acad. Sci. (USA) 99:10843-10848 (2002), which is incorporated herein by reference). Thus, the sequences of the invention can also be used in the treatment of Alzheimer's disease.

TABLE 1

Clusterin RNAi Sequences

| Target region of cDNA (nt) | 487-505 | 1105-1123 | 1620-1638 |
|---|---|---|---|
| sense siRNA | ccagagcucgcccuucuac-dtdt (SEQ. ID No: 1) | gaugcucaacaccuccucc-dtdt (SEQ ID No: 3) | cuaauucaauaaaacuguc-dtdt (SEQ. ID No: 5) |
| antisense siRNA | guagaagggcgagcucugg-dtdt (SEQ. ID No: 2) | ggaggagguguugagcauc-dtdt (SEQ. ID No: 4) | gacaguuuuauugaauuag-dtdt (SEQ. ID No: 6) |

TABLE 1-continued

Clusterin RNAi Sequences

| Target region of cDNA (nt) | HIV 1152-1176 | 53-71 | not sequence specific |
|---|---|---|---|
| sense siRNA | uaauucaacaaaacugu-dtdt (SEQ. ID No: 7) | augaugaagacucugcugc-dtdt (SEQ. ID No: 9) | ugaaugaagggacuaaccug-dtdt (SEQ. ID No: 11) |
| autisense siRNA | acaguuuuguugaauua-dtdt (SEQ. ID No: 8) | gcagcagagucuucaucau-dtdt (SEQ ID No: 10) | cagguuaguccccuucauuca-dtdt (SEQ. ID No: 12) |

| Target region of cDNA (nt) | not sequence specific | not sequence specific | |
|---|---|---|---|
| sense siRNA | cagaaauagacaaagugggg-dtdt (SEQ. ID No: 13) | acagagacuaagggaccaga-dtdt (SEQ. ID No: 15) | |
| antisense siRNA | ccccacuuugucuauuucug-dtdt (SEQ. ID No: 14) | acagagacuaagggaccaga-dtdt (SEQ. ID No: 16) | |

Specific results relating to the use of the RNAi species shown in Table 7 are shown in the Figures. These results demonstrate the effectiveness of clusterin suppression by RNAi mediated processes to reduce the growth of and to promote apoptosis in osteosarcoma cells, thus demonstrating a further type of condition which can be treated in accordance with the invention. The results also demonstrate that RNAi treatment to reduce clusterin levels results in increased levels of p53 and reduced levels of bcl-2 Thus, in accordance with the invention, conditions in which active p53 or bcl-2 levels are affected due to regulation as opposed to a mutation that renders the tumor suppressor wholly or partially inactive are overcome by administration of an amount of clusterin RNAi effective to reduce the amount of clusterin present, and thus the undesirable clusterin-associated modulation of p53 and bcl-2 levels.

A second group of RNA molecules in accordance with the present invention are directed to mRNA encoding insulin-like growth factor binding protein-5 (IGFBP-5). It has been shown that inhibition of IGFBP-5 expression can delay the progression of hormone-regulated (prostatic or breast) tumor cells to hormone (e.g. androgen or estrogen) independence, provide a therapeutic method for the treatment of individuals, including humans, suffering firm hormone regulated cancers, such as breast or prostate cancer and inhibit or delay the growth and metastatic progression of prostate, breast and other IGF-1 sensitive tumors in bone. (Published PCT Application No. WO01/05435, which is incorporated herein by reference.) These same results are obtained using RNAi therapy in accordance with the invention using siRNA molecules having the sequences set forth in Table 2. These sequences can be used alone or in combination with other chemotherapy agents or apoptosis inducing treatment concepts.

TABLE 2

IGBFP-5 RNAi Sequences

| Target region of cDNA (nt) | 44-61 | 876-895 | not sequence specific |
|---|---|---|---|
| sense siRN | augguguugcucaccgcg-dtdt (SEQ. ID No: 17) | cccugggcugcgagcugguc-dtdt (SEQ. ID No: 19) | tgaggaaacugaggaccucgg-dtdt (SEQ. ID No: 21) |
| antisense siRNA | cgcggugagcaacaccau-dtdt (SEQ. ID No: 18) | gaccagcucgcagcccaggg-dtdt (SEQ. ID No: 20) | ccgagguccucaguuuccuc-dtdt (SEQ. ID No: 22) |

| Target region of cDNA (nt) | not sequence specific | 850-568 | 1225-1243 |
|---|---|---|---|
| sense siRNA | cucggauucucaugcaaggg-dtdt (SEQ. ID No: 23) | agcccucuccaugugcccc-dtdt (SEQ. ID No: 25) | gaagcugacccaguccaag-dtdt (SEQ. ID No: 27) |
| antisense siRNA | cccuugcuagagauuccgag-dtdt (SEQ. ID No 24) | gggcacauggagagggcu-dtdt (SEQ. ID No: 26) | cuuggacugggucagcuuc-dtdt (SEQ ID No: 28) |

| Target region of cDNA (nt) | 1501-1520 | | |
|---|---|---|---|
| sense siRNA | gcugccaggcauggaguacg-dtdt (SEQ. ID No: 29) | | |
| antisense siRNA | cguacuccaugccuggcagc-dtdt (SEQ. ID No 30) | | |

A third group of RNA molecules in accordance with the present invention are directed to mRNA encoding insulin-like growth factor binding protein-2 (IGFBP-2). It has been shown that inhibition of expression of IGFBP-2 delays the progression of prostatic tumor cells to androgen independence, and provides a therapeutic benefit for mammalian individuals, including humans, suffering from hormone-regulated cancer such as prostate or breast cancer. In addition, the compositions of the invention can be used to inhibit or delay the growth and metastatic progression of such cancers. (Published PCT Application No. WO02/22642, which is incorporated herein by reference). These same results are obtained using RNAi therapy in accordance with the invention using siRNA molecules having the sequences set forth in Table 3. These sequences can be used alone or in combination with other chemotherapy agents or apoptosis inducing treatment concepts.

TABLE 3

IGFBP-2 RNAi Sequences

| Target region of cDNA (nt) | 118-138 | 1393-1411 | 906-924 |
|---|---|---|---|
| sense siRNA | augcugccgagagugggcugcd-TdT (SEQ. ID No: 31) | ccccuguguccccuuuugca-dTdT (SEQ. ID No: 33) | cugugacaagcauggccug-dTdT (SEQ. ID No: 35) |
| antisense siRNA | gcagcccacucucggcagcau-dTdT (SEQ. ID No: 32) | ugcaaaagggacacagggg-dTdT (SEQ. ID No: 34) | caggccaugcuugucacag-dTdT (SEQ. ID No: 36) |

| Target region of cDNA (nt) | 525-542 |
|---|---|
| sense siRNA | gcgccgggacgccgagua-dTdT (SEQ. ID No: 37) |
| antisense siRNA | uacucggcgucccggcgc-dTdT (SEQ. ID No: 38) |

A fourth group of RNA molecules in accordance with the present invention are directed to mRNA encoding insulin-like growth factor-2 and 5 simultaneously (IGF-Bis). Inhibition of expression of both IGFBP-2 and IGFBP-5 can delay the progression of hormone-regulated (prostatic or breast) tumor cells to hormone (e.g. androgen or estrogen) independence, provide a therapeutic method for the treatment of individuals, including humans, suffering from hormone regulated cancers, such as breast or pro state cancer and inhibit or delay the growth and metastatic progression of prostate, breast and other IGF-1 sensitive tumors in bone potentially more effectively than the inhibition of either of these factors (Published PCT Application No. WO01/05435, Published PCT Application No. WO02/22642, and U.S. Provisional Application No. 60/350,046, filed Jan. 17, 2002, which are incorporated herein by reference.) These same results are obtained using RNAi therapy in accordance with the invention using siRNA molecules having the sequences set forth in Table 4. These sequences can be used alone or in combination with other chemotherapy agents or apoptosis inducing treatment concepts.

TABLE 4

IGFBP-2 and IGFBP-5 Bispecific RNAi Sequences

| Target region of cDNA (nt) | BP5- 898-919<br>BP2 346-362 | BP5 948-964<br>BP2 416-432 | BP5 976-991<br>BP2 444-459 |
|---|---|---|---|
| sense siRNA | ggagccgggcugcggcugc-dtdt (SEQ. ID No: 39) | cgugcggcgucuacacc-dtdt (SEQ. ID No 41) | ccaggggcugcgcugc-dtdt (SEQ. ID No: 43) |
| antisense siRNA | gcagccgcagcccggcucc-dtdt (SEQ. ID No: 40) | gguguagacgccgcacg-dtdt (SEQ. ID No: 42) | gcagcgcagcccugg-dtdt (SEQ. ID No: 44) |

A fifth group of RNA or DNA antisense molecules in accordance with the present invention are directed to mRNA encoding the group of microphthalmia transcription factors (Mitf). Bcl-2 is regulated in melanoma and other cells by the master regulator Mitf which has been reported to modulate melanoma cell viability, lineage survival, and susceptibility to apoptosis (McGill et al. (2002) Cell 109, 707-718, incorporated herein by reference). Mitf and Bcl-2 regulated by Mitf are expressed in increased amounts by various human tumors. RNAi or antisense therapy which reduces the expression of Mitf may provide therapeutic benefits in the treatment of cancer. In accordance with the invention, Mitf can also enhance sensitivity of cancer cells to chemotherapeutic agents and to radiotherapy both in vitro and in vivo. Sequences of specific antisense or RNA molecules which may be used to interfere with the expression of Mitf are listed in Table 5. These sequences can be used alone or in combination with other chemotherapy agents or apoptosis inducing treatment concepts in the treatment of melanoma, prostate cancer, renal cell carcinoma, bladder cancer, lung cancer, bone cancer and other tumors.

The siRNA molecules of the invention are used in therapy to treat patients, including human patients, that have cancers or other diseases of a type where a therapeutic benefit is obtained by the inhibition of expression of the targeted protein. siRNA molecules of the invention are administered to patients by one or more daily injections (intravenous, subcutaneous or intrathecal) or by continuous intravenous or intrathecal administration for one or more treatment cycles to reach plasma and tissue concentrations suitable for the regulation of the targeted mRNA and protein.

EXAMPLE 1

Protocol for Transfection of LNCaP and PC3 cells with siRNA Duplexes

1) Cell Preparation

In each well of 6-well plate seed $0.5 \times 10^6$ of LNCaP cells [PC3 cell at the density $0.3 \times 10^6$ per well] in appropriate media containing 5% FBS without antibiotics [penicillin/streptomycin]

Incubate the cells at 37° C. in a humidified 5% CO2 incubator until they reach 40-50% confluence.

TABLE 5

Mitf RNAi Sequences

| Target region of cDNA (nt) | 207-225 | 1287-1305 | 2172-2190 |
|---|---|---|---|
| sense siRNA | ccgcugaagagcagcaguu-dtdt (SEQ. ID No: 45) | augcaggcucgagcucaug-dtdt (SEQ. ID No: 47) | agauacaguaccccucuag-dtdt (SEQ. ID No: 49) |
| antisense siRNA | aacugcugcucuucagcgg-dtdt (SEQ. ID No: 46) | caugagcucgagccugcau-dtdt (SEQ. ID No: 48) | cuagagggguacuguaucu-dtdt (SEQ. ID No: 50) |

A sixth group of RNA or DNA antisense molecules in accordance with the present invention are directed to mRNA encoding B-raf. B-raf is a key player in cellular signal transduction and is activated by somatic missense mutations in 66% of malignant melanomas and at lower frequencies in a wide range of human cancers (Davies et al. (2002) Nature 417, 949-954, incorporated herein by reference). RNAi or antisense therapy which reduces the expression of activated and/or non-activated B-raf may provide therapeutic benefits in the treatment of cancer. In accordance with the invention, reduction in expression of B-raf can also enhance sensitivity of cancer cells to chemotherapeutic agents and to radiotherapy both in vitro and in vivo. Sequences of specific antisense or RNA molecules which may be used to interfere with the expression of B-raf are listed in Table 6. These sequences can be used alone or in combination with other chemotherapy agents or apoptosis inducing treatment concepts in the treatment of melanoma, prostate cancer, renal cell carcinoma, bladder cancer, lung cancer, bone cancer and other tumors.

2) si RNA Preparation

Prepare the following si RNA dilution in microcentrifuge tubes. For each well: 0.01-100 nM 3) Prepare the Following Transfection Reagent Dilution in Microcentrifuge Tubes For each well of 6-well plate dilute 4 ml of OligoFECTAMINE™ Reagent into 11 ml of OPTI-MEM™ and incubate 10 min at room temperature 4) Combine the diluted OligoFECTAMINE™ to the diluted siRNA duplexes and mix gently by inversion 5) Incubate 20 min at room temperature 6) Remove the media from the well and replace it with 800 nm of Opti-MEM™

7) Overlay the 200 ml of transfection complexes onto the cells

8) Incubate 4 hrs at 37 degrees C. in a $CO_2$ incubator 9) add 500 ml of media containing 15% FBS 10) after 24 hrs check gene expression by Real Time PCR or 11) check protein expression with Western Blot after 1, 6, 12, 24, 48, 72 and 96 hours

TABLE 6 b-raf RNAi Sequences

| Target region of cDNA (nt) | 362-380 | 1184-1202 | 2249-2267 |
|---|---|---|---|
| sense siRNA | ucucugggguucgguucug-dtdt (SEQ. ID No: 51) | ccugucaauauugaugacu-dtdt (SEQ. ID No: 53) | cccuccuuguuucgggcug-dtdt (SEQ. ID No: 55) |
| antisense siRNA | caguccguuccccagaga-dtdt (SEQ. ID No: 52) | agucaucaauauugacagg-dtdt (SEQ. ID No: 54) | cagcccgauucaaggaggg-dtdt (SEQ. ID No: 56) |

EXAMPLE 2

The human clusterin cDNA was manually scanned in order to identify sequences of the AA(N$_{19}$)UU (N, any nucleotide) type that fulfill the required criteria for siRNA (Harbourth et al., J Cell Sci 114:4557-4560 (2001)). Two such sequences with symmetric 2-nt 3' overhangs, were found 433 (Cl-I) and 644 (Cl-II) nts downstream of the CLU gene transcription initiation codon. Two additional oligonucleotides used targeted a region 1620 nts downstream of the CLU gene transcription initiation codon (Cl-III) and the human CLU transcription initiation site (Cl-V) (see Table). BLAST analysis showed no homology with other known human genes. Selected RNA oligos were synthesized by Dharmacon Research, Inc. (Lafayette, CO), diluted at a 20 µM final concentration in RNasefree ddH$_2$O and stored at −20° C. The Scramble-I™ (Sc-I) (D-1200-20) and Scramble-II™ (Sc-II) (D-1205-20) oligonucleotides used were purchased from Dharmacon Research, Inc.

siRNA transfection of the Cl-I, Cl-II and scrambled RNA duplexes in exponentiary growing OS cells was performed as described (Harbourth et al., Tuscl et al., Genes Dev. 13:3191-3197 (1999)). Briefly, cells were seeded the day before siRNA transfection in 24-well plates containing 500 µl complete medium and were ~40-50% confluent during transfection. For the transfection mixture 100 nM of siRNA duplex per well were used. The RNA duplex was diluted in Opti-MEM® I (Gibco Life Technologies, Inc., San Diego, CA) serum free medium and transfection efficiency was enhanced by using the Oligofectamine™ reagent (Invitrogen Life technologies Inc., San Diego, CA). When cells were treated with both Cl-i and Cl-II oligonucleotides, 100 nM of each siRNA duplex were used. Cell treatment with the siRNA oligonucleotides lasted for 2-3 days.

Alternatively, in PC3 cells Lipofectin™ (Invitrogen Life technologies Inc., San Diego, CA) was used to enhance transfection with the Cl-III and CL-V oligonucleotides. PC3 cells were treated with 10, 50, or 100 nM of the RNA duplexes after pre-incubation with 4 µg/ml of Oligofectamine™ reagent in serum free OptiMEM® I for 20 minutes. Four hours after starting the incubation, the medium containing the RNA duplexes and Lipofectin was replaced with standard tissue culture medium. Cells were treated once on day 1 and then harvested 48 h after treatment on day 3. In all cases controls used included: (a) the usage of the Sc-I and Sc-II RNA duplexes and (b) mock transfections in the absence of a nucleic acid (Con-I). CLU gene silencing was assayed by RNA blot analysis, inuunoblotting analysis or confocal immunofluorescence.

Efficient silencing of the CLU gene expression in OS cells is achieved using siRNA. Treatment of the three OS cell lines with the Cl-I or the Cl-II siRNA oligonucleotides appeared to be quite effective and resulted in knocking down significantly the cellular CLU protein levels. Interestingly, the Cl-I oligonucleotide appeared to be slightly more effective than Cl-II in silencing the CLU gene. No CLU gene silencing was seen in the presence of the control Sc-I or the Sc-II oligonucleotides or at the absence of RNA duplexes from the transfection medium.

Next we addressed the issue of whether the CLU-specific siRNA oligonucleotides could also inhibit the accumulation of the CLU protein following cellular exposure to DXR. Exposure of the KH OS and U-2 OS cells to DXR for 24 h in the presence of the Cl-I, Cl-II or a mixture of both the Cl-I, Cl-II oligonucleotides effectively abolished CLU protein accumulation. It is thus evident that in the presence of the Cl-I or the CI-II oligonucleotides the cellular CLU protein cannot be induced after cell exposure to apoptosis inducing agents.

EXAMPLE 3

Figure 1B:
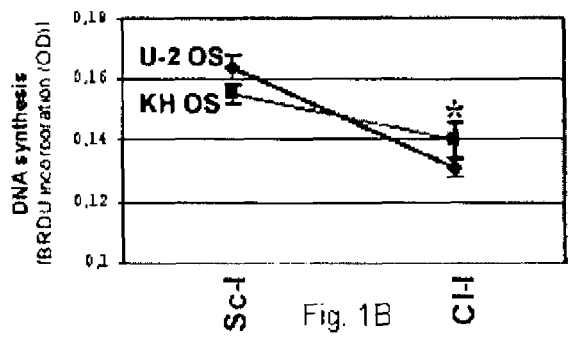
FIGS. 1B and C show endogenous DNA synthesis levels and spontaneous apoptosis in clusterin knock down KH OS and U-2 OS cells, as estimated by cell proliferation ELISA BrdU colorimetric immunoassay and a Cell Death detection ELISA photometric enzyme immunoassay, respectively. Clusterin knock-down was accompantied by reduced DNA synthesis and an enhanced rate of endogenous spontaneous apoptosis in both cell lines.
Figure 1C:
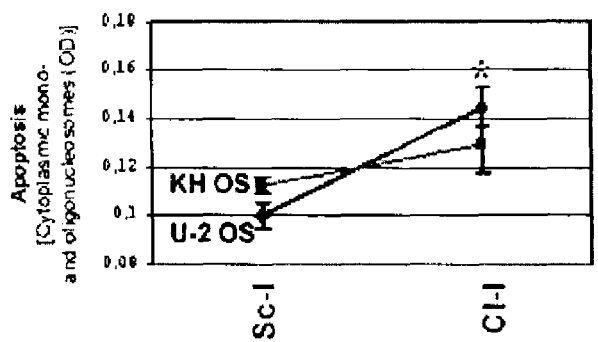

Phenotypic effects in OS cells following CLU gene expression silencing by siRNA. The effects of CLU gene expression silencing in OS cells were studied by direct counting of the cells following siRNA, by recording cellular morphology and phenotype, as well as by clonogenic assays. CLU knock down in KH OS and Sa OS cells did not result in any visible phenotype. However, the CLU knock down cells were found to be significantly growth retarded as compared to their control counterparts (FIG. 1A). In contrast at the U-2 OS cells, that express the higher endogenous amount of the CLU protein, the effects of CLU knock down appeared quite significant. Specifically, CLU siRNA treated (for three days) U-2 OS cells lost their fit adherence to plastic and acquired a rounding shape. This phenotype was accompanied by a severe growth retardation effect. In order to study whether a combination of both Cl-I and Cl-II RNA duplexes would be more effective in inhibiting cell growth, we treated cells with both these oligonucleotides. For the KH OS and U-2 OS cells, only a slight increase in growth retardation was observed as compared to the Cl-I treated cells. Finally, in order to distinguish between the cytostatic and cytotoxic effects of CLU protein elimination we directly assayed CLU knock down KH OS and U-2 OS cells for DNA synthesis and endogenous spontaneous apoptosis. CLU knock down cells showed a reduced DNA synthesis rate (FIG. 1A) and higher levels of endogenous spontaneous apoptosis (FIG. 1B) as compared to their sibling controls. Effects were again more pronounced in U-2 OS cells. In summary, these results suggest that the reduced number of CLU knock down cells is due to a reduced rate of cell proliferation as well as to an increased level of spontaneous apoptosis.

Figure 2A:
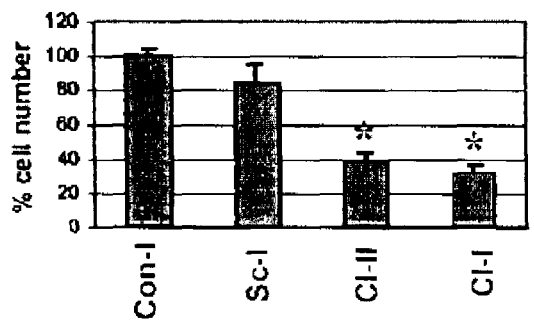
FIGS. 2A and B show reduced clonogenic potential of clusterin knock down OS cells. After siRNA treatment for 70 hours, $5\times10^3$ KH OS cells were seeded in 6 well plates, and the total number of cells was counted after 5 days of growth in complete medium (FIG. 2A).
Figure 2B:
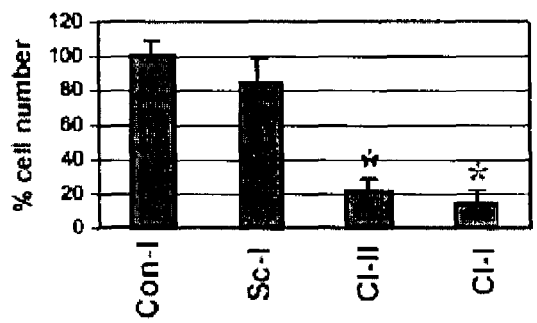
FIG. 2B shows the results of a conparable experiment with U-2 OS cells.

The effect of CLU knock down in plating efficiency and growth following siRNA was also studied by clonogenic assays as recent studies have demonstrated that gene silencing is sustained for more than 7 cellular doublings (Harbourth et al.). KH OS and U-2 OS cells were selected for these assays since they represent two extreme opposite cases as far as the endogenous CLU amount and the intensity of CLU accumulation during stress are concerned. CLU knock-down KH OS cells when plated were firmly attached to the plastic (more than 90% of the seeded cells were attached) and only a few of the attached cells showed an abnormal morphology. However, the growth potential of the adherent cells was impaired as found 5 days post-plating after analyzing the total colony number and size of the formed colonies (FIG. 2A). CLU knocked-down U-2 OS cells were poorly attached to the plastic after trypsinization (only~70% of the seeded cells were attached) and most of the adherent cells appeared quite abnormal in shape. Cells showed an extremely low proliferation potential (FIG. 2B) and after 9 days in culture only some small colonies could be seen.

EXAMPLE 4

Sustained silencing of CLU gene expression in OS cells by siRNA results in significant sensitization to apoptosis induced by genotoxic and oxidative stress. Prior to CLU functional assays, we analyzed the DXR effects in OS cells since the drug-related reported effects vary in different cell-types (Gewritz et al., Biochem Pharmacol. 57:727-741 (1999)). As the DXR plasma concentration in treated patients fall into a range of 1-2 µM and decline into a range of 0.025-

0.25 µM within 1 h (Muller et al, Cancer Chemother. Pharmacol., 32:379-384 (1993)) cells were treated with 0.35 and 1 µM of DXR. To analyze the extent of the DXR-mediated cell death we scored apoptosis by TUNEL. Attached cells following drug treatment for 24 h underwent significant morphological changes as compared to non-treated control cells. At this time cells exhibit an enlarged and flattened morphology that is reminiscent of a senescence-like phenotype, while a significant number of them are TUNEL positive. On-going apoptosis is also apparent 24 h later, verifying that apoptosis is a dynamic process that continues even after DXR removal from the medium In agreement with the results obtained by TUNEL, DXR treatment was accompanied by PARP cleavage; the anti-apoptotic protein bcl-2 showed no altered expression in drug-treated KH OS and U-2 OS cells. Following DXR treatment, accumulation of p53 protein and its downstream effectors related to either growth arrest (p21) or apoptosis (bax) was found only in U-2 OS cells indicating that the cytostatic and cytotoxic effects mediated by DXR in OS cell lines rely on both p53-dependent and p53-independent mechanisms.

Figure 3A:
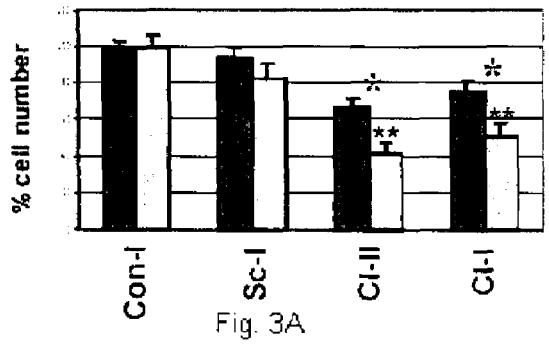
FIGS. 3A-F show the effect of DXR treatment in OS cells and cell sensitization to DNA damage and oxidative stress following siRNA-mediated clusterin knock down. The dark bars in FIGS. 3A and B show the results when $2\times10^4$ KH OS or U-2 OS cells were seeded in 6 well plates in complete medium, siRNA treated for 70 hours and then allowed to recover. The cells were then exposed to 0.35 μM DXR for 24 hours, sub-cultured in complete medium for 72 hours and counted. The light bars in FIGS. 3A and B show the results when $2\times10^4$ KH OS or U-2 OS cells were seeded in 6 well plates in complete medium, siRNA treated for 70 hours and DXR was added directly to the transfection medium to a final concentration of 0.35 μM. Cells were incubated in the drug containing transfection medium for 24 hours, washed, allowed to recover in complete medium for 72 hours and counted.
Figure 3B:
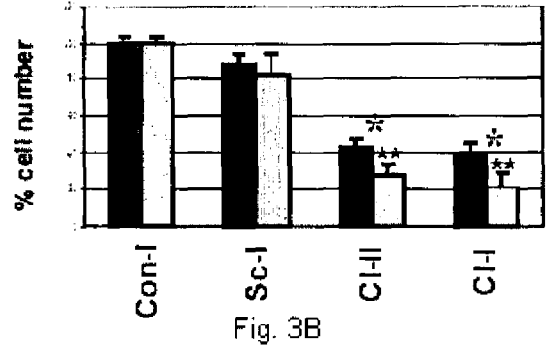
Figure 3C:
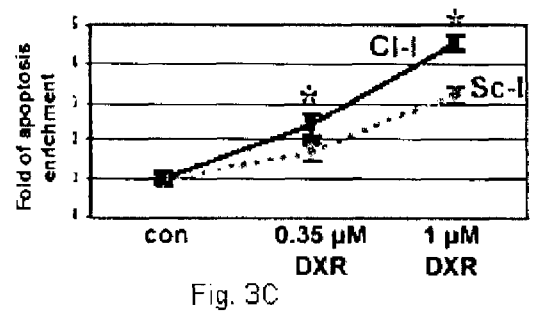
Figure 3D:
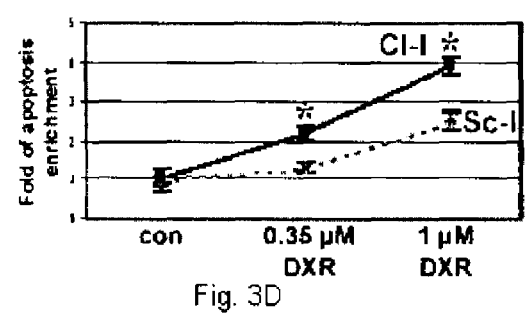
Figure 3E:
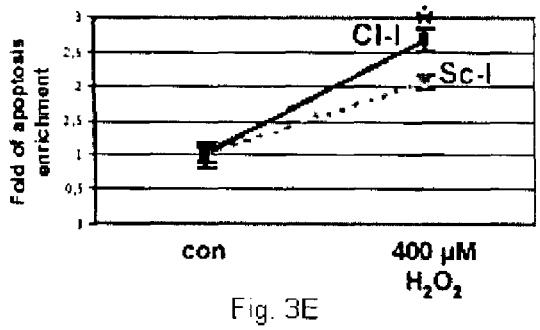
Figure 3F:
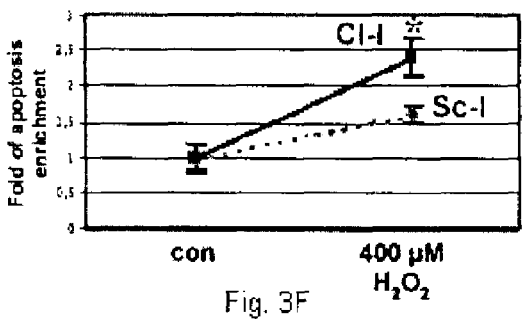

Next, we followed two complementary approaches to study the effect of CLU knock down in OS cells exposed to DXR (FIGS 3A and B). SiRNA treated cells were either replated in complete medium and were subsequently exposed to 0.35 µM DXR for 24 h, or they were exposed to 0.35 µM DXR in the presence of the Cl-II or Cl-I oligonucleotides. In both cases viable cells were counted 3 days post-DXR treatment. CLU knocked-down KHr OS cells appeared more sensitive to DXR than their control counterparts (FIG. 3A-*dark* bars), whereas DXR treatment appeared significantly more effective when it was combined with the presence of the CLU-specific siRNA oligonucleotides in the medium (FIG. 3A-*light* bars). Similarly, CLU knocked-down Sa OS cells were more sensitive to the DXR treatment. In U-2 OS cells both strategies appeared very effective and CLU knock-down cells were significantly more sensitive to the drug as compared to controls (FIG. 3B). When DXR treatment was performed in the presence of the CLU-specific siRNA oligonucleotides, the CLU knock-down cells appeared to he significantly more sensitive to the drug (FIG. 3B-*light* bars) and a massive apoptosis was observed. Finally, when U-2 OS cells were treated with both the Cl-I and Cl-II oligonucleotides, cells were almost eliminated.

To understand the mechanism of cell sensitization following CLU knock down, we directly assayed the intensity of apoptosis induction right after cell exposure to agents inducing genotoxic (DXR) or oxidative stress ($H_2O_2$). As shown in FIG. 3C-F. Exposure of the CLU knock-down cells to either DXR or $H_2O_2$ resulted in a significantly higher rate of apoptosis in both KH OS and U-2 OS cells. This observation suggests that CLU directly affects or interacts with the cellular machinery involved in apoptosis, by providing cytoprotective signals.

EXAMPLE 5

OS cells sensitization to genotoxic and oxidative stress due to CLU gene silencing is related to activation of the cellular apoptotic machinery. By analyzing the expression levels of other recently identified CLU protein forms, to our surprise, we found that the Cl-I and CI-II oligonucleotides did not exert any significant effect on the putative 55 kDa n-CLU[35] CLU protein form in both KH OS and U-2 OS cells; a minor effect on the 49 kDa c-CLU[49] protein form level was detected despite the fact that the binding sites of the Cl-I or Cl-II oligonucleotides are common between the s-CLU and n-CLU mRNAs (Leskov et al., J. Biol. Chem 278:11590-16000 (2003)). We assume that the explanation of this effect relies on our observation that the n-CLU protein is extremely stable. Thus CL-I and CL-II oligonucleotides specifically knock-down the secreted CLU (s-CLU) protein form We then assayed the expression levels of several proteins involved in regulating apoptosis in human cells. CLU knock down in both KH OS and U-2 OS cells resulted in the down-regulation of the anti-apoptotic molecule bcl-2. No effect was detected on levels of Ku70, a protein implicated in DNA damage repair and signaling that, moreover, binds n-CLU (Yang et al., Proc. Nat'l Acad. Sci (USA) 97:5907-5912 (2000)). Interestingly, in U-2 OS cells, which bear a functional p53 molecule, CLU knock down apart from bcl-2 down-regulation is also accompanied by p53 accumulation and up-regulation of its downstream pro-apoptic effector, bax. Supportively, CLU knock-down U-2 OS cells when exposed to DXR showed a more intense and robust accumulation of the p53 protein as compared to the Sc-I treated cells. We suggest that sensitization of OS cells following CLU knock down largely depends on the activation of the cellular pro-apoptotic machinery. On-going studies in our laboratories are investigating the implication of CLU on the cell signaling cascades related to apoptosis regulation.

EXAMPLE 6

Figure 4:
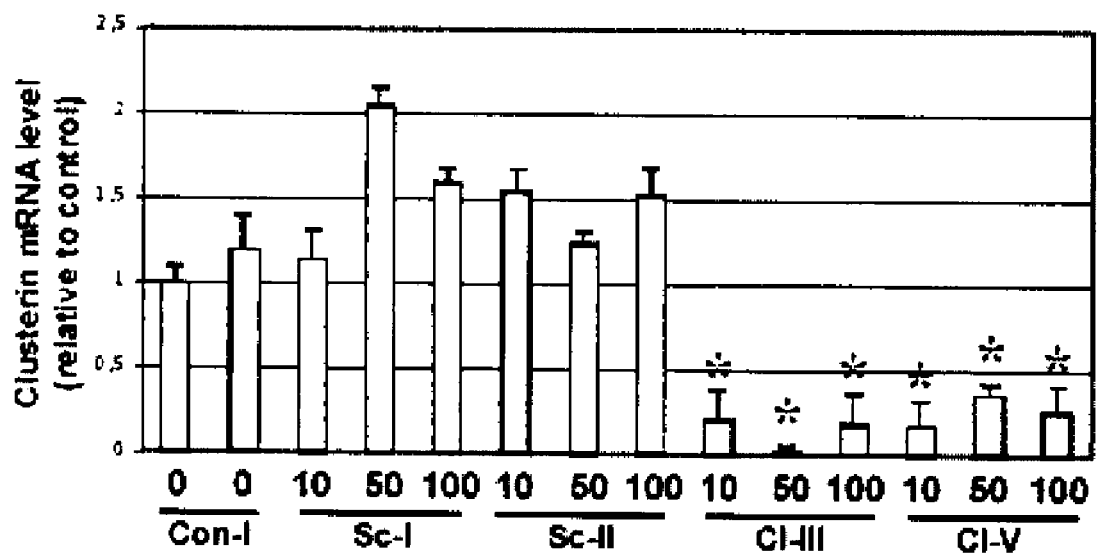
FIG. 4 shows quantitiative analysis of sequence-specific clusterin gene silencing by siRNA in PC3 tumor cells.

Effects of CLU gene silencing in PC-3 prostate cancer cells were determined. Having established the significant effects of CLU knock down in OS cells, we then applied CLU siRNA in PC3 human prostate cancer cells. PC3 cells are p53 null (Rohlff, et al., Prostate 37:51-59 (1998)) and express relatively low endogenous amount of the s-CLU protein form similar to the Sa OS cells. In PC3 cells, apart from employing the Cl-I and CL-II oligonucleotides, we also tested two additional CLU-specific siRNA oligonucleotides (Cl-III, Cl-V). From these oligos, Cl-V targeted the s-CLU transcription initiation site. Usage of the Cl-I and Cl-II oligonucleotides in PC3 cells resulted in similar effects to those described for OS cell lines. As it can been seen in FIG. 4 both the Cl-Ill and Cl-V oligonucleotides are quite effective in silencing CLU RNA and protein expression in a sequence-dependent but dose-independent manner. More specifically, treatment of the PC3 cells, for one day, with 10, 50 and 100 nM of either Cl-Ill or Cl-V siRMN oligonucleotides severely reduced CLU mRNA levels ranging from 60% to 98% (FIG. 4). This effect on mRNA levels was also evident at protein level. Additionally and in agreement with findings in the U-2 OS cells, CLU knock down in PC3 cells resulted in significant morphologic changes that resembled an on-going apoptosis.

Figure 5:
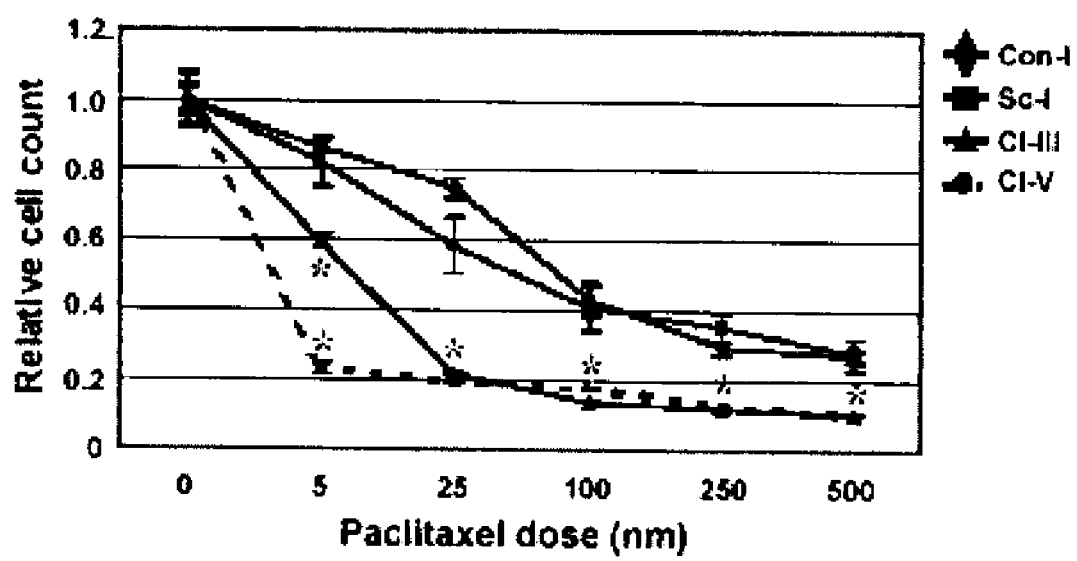
FIG. 5 shows the effects of paclitaxel treatment on clusterin knock down PC3 cell growth and apoptosis. Cells were treated with 50 nM of the Cl-III, Cl-IV or scrambled control siRNA for 1 day. Two days following the siRNA treatment, cells were exposed to the indicated concentrations of paclitaxel for 48 hours, and cell viability was determined by an in vitro MTT assay.

To determine whether treatment of PC3 cells with CLU siRNA oligonucleotides could enhance the cytotoxic effects of chemotherapeutic drugs, PC3 cells were treated first with the Cl-III, Cl-V or the Sc-I siRNA oligonucleotides and then incubated with medium containing various concentrations of Paclitaxel for 2 days. An MTT assay was then performed to determine cell viability. As shown in FIG. 5, CLU siRNA treatment significantly enhanced chemosensitivity of Paclitaxel in a dose-dependent manner reducing the $IC_{50}$ (the concentration that reduces cell viability by 50%) of Pachtaxel by more than 90%, whereas the scrambled siRNA had no effect.

TABLE 7

Sequence specific characteristics of the Cl-I, Cl-II,
CL-III and Cl-V oligonucleotides. The Cl-I, Cl-II, Cl-III
and Cl-IV clusterin specific siRNA oligonucleotides have
GC/AT ratios of 57/43 67/33, 24/76 and 43/57,
respectively.

|  | Cl-I | Cl-II |
|---|---|---|
| Targeted region | AAccagagctcgcccttctacTT (SEQ ID No: 57) | AAgtcccgcatcgtccgcagcTT (SEQ. ID No: 60) |
| Sense siRNA | ccagagcucgcccuucuacdTdT (SEQ. ID No: 58) | gucccgcaucguccgcagcdTdT (SEQ. ID No: 61) |
| Antisense siRNA | guagaagggcgagcucuggdTdT (SEQ. ID No: 59) | gcugcggacgaugcgggacdTdT (SEQ. ID No: 62) |
|  | Cl-III | Cl-IV |
| Targeted region | AActaattcaataaaactgtcTT (SEQ. ID No: 63) | GCatgatgaagactctgctgcTG (SEQ. ID No: 66) |
| Sense siRNA | cuaauucaauaaaacugucdTdT (SEQ. ID No: 64) | augaugaagacucugcugc (SEQ. ID No: 67) |
| Antisense siRNA | gacaguuuuauugaauuagdTdT (SEQ. ID No: 65) | gcagcagagucaucaucau (SEQ. ID No: 68) |

EXAMPLE 7

8 species of siRNA targeting clusterin were formed as double-stranded RNA from Seq. ID NOs. 1 and 2, 3 and 4, 5 and 6, 7 and 8, 9 and 10, 11 and 12, 13 and 14, and 15 and 16, and labeled as CLU 1-CLU 8, respectively. PC3 cells were transfected with various doses (10, 50 and 100 nM) of the 8 species of siRNA or scrambled control. Three days after treatment, proteins were extracted and analyzed by Western blotting for clusterin levels (MW=40 and 60 kDa). Reduction in the amount of clusterin was observed with all eight species of siRNA, although the best results were obtained with CLU-5 (Seq ID Nos 9 and 10).

Figure 6:
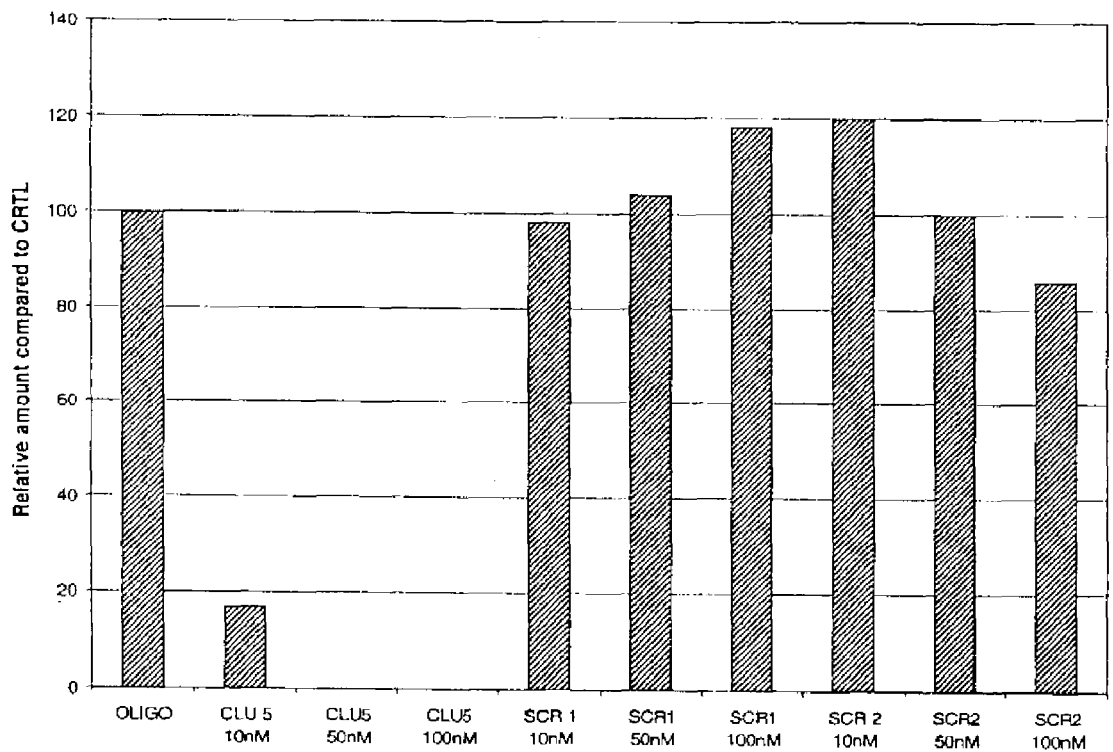
FIG. 6 shows quantitative results of exposure of PC3 prostate cancer cells to CLU-5 siRNA (Seq ID NOs. 9 and 10).

Densitometric measurements were performed after normalization to a vinculin control the blots for cells treated with CLU-5 (Seq ID Nos. 9 and 10). The results are summarized in FIG. 6. "Oligo" cells were treated with oligoFECTAMINE™ only. As can be seen, a dose dependent response to the siRNA was observed.

EXAMPLE 8

Figure 7:
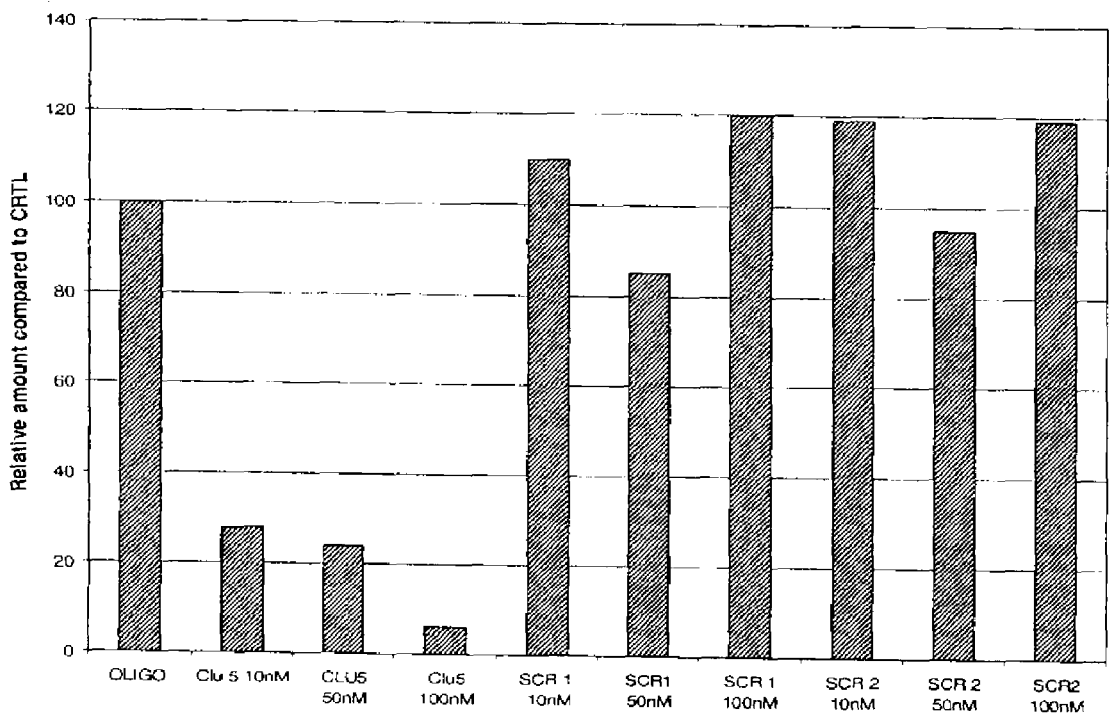
FIG. 7 shows quantitative results of exposure of A549 lung cancer cells to CLU-5 siRNA (Seq ID NOs. 9 and 10).

The experiment of Example 7 was repeated using A549 lung cancer cells in place of PC3 prostate cells, and comparable results were observed. Densitometric measurements were performed after normalization to a vinculin control the blots for cells treated with CLU-5 (Seq ID Nos. 9 and 10). The results are summarized in FIG. 7. "Oligo" cells were treated with oligoFECTAMINE™ only. As can be seen, a dose dependent response to the siRNA was observed.

EXAMPLE 9

Figure 8:
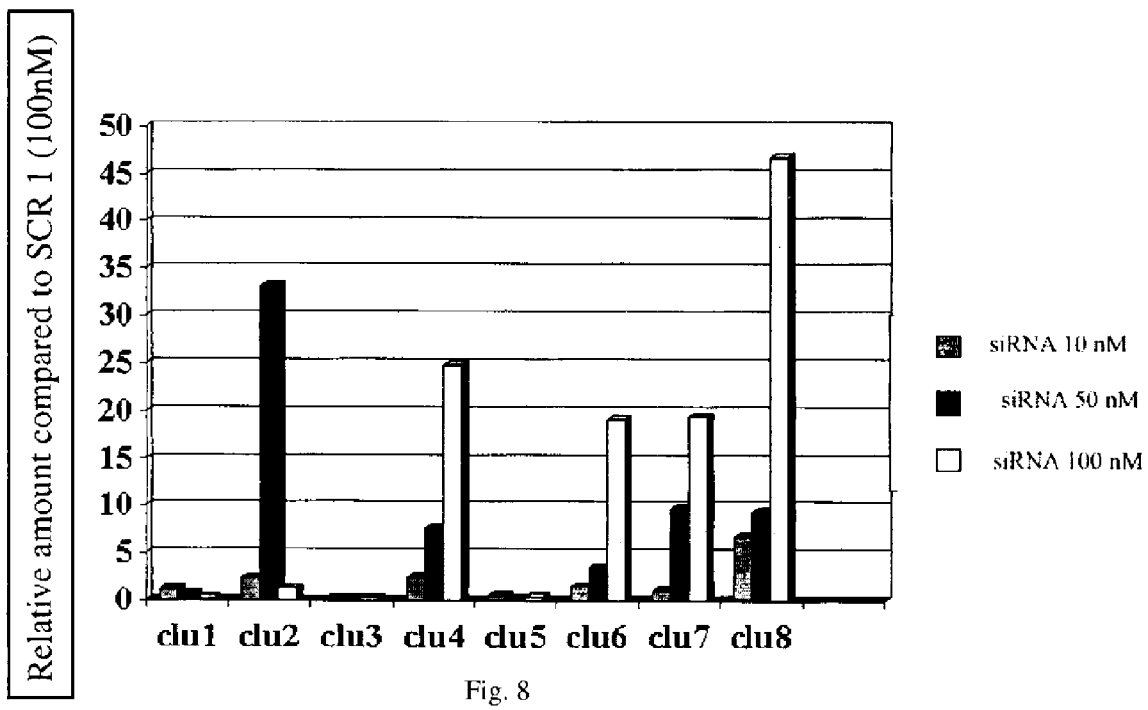
FIG. 8 shows the reduction in clusterin transcript as a result of treatment of PC3 cells with clusterin-targeted siRNA as determined by RT-PCR.

PC3 cells were transfected with siRNA at levels of 10, 50 or 100 nM or with 100 nM scrambled control. Two days after transfection, total RNA was extracted and the level of clusterin transcript was quantified by Real Time PCR. The results are shown in FIG. 8. As can be seen, each of the 8 species of siRNA tested resulted in a reduction in the amount of clusterin transcript.

EXAMPLE 10

Figure 9:
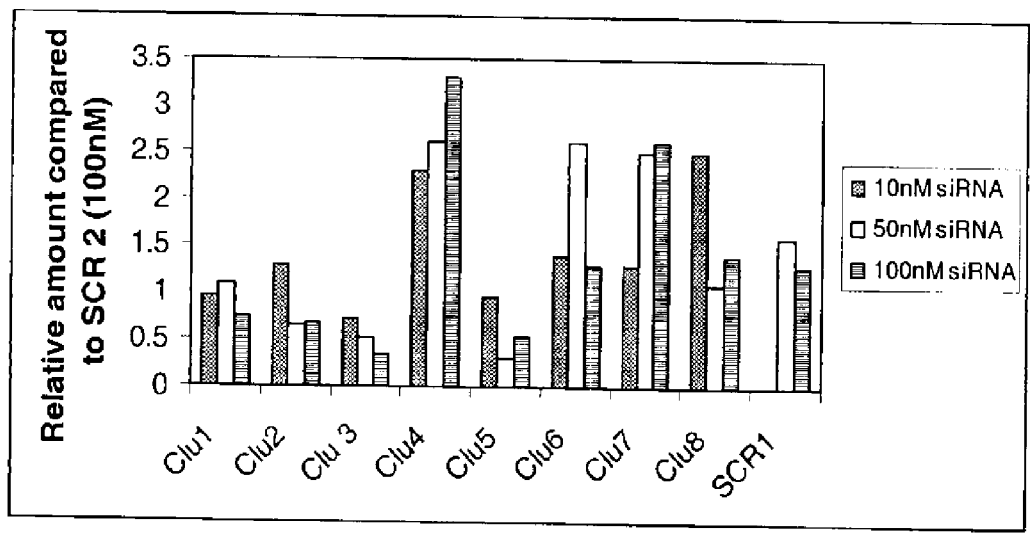

The experiment of Example 9 was repeated using A549 cells in place of PC3 cells. The results are shown in FIG. 9. As can be seen, each of the 8 species of siRNA tested resulted in a reduction in the amount of clusterin transcript.

EXAMPLE 11

Figure 10:
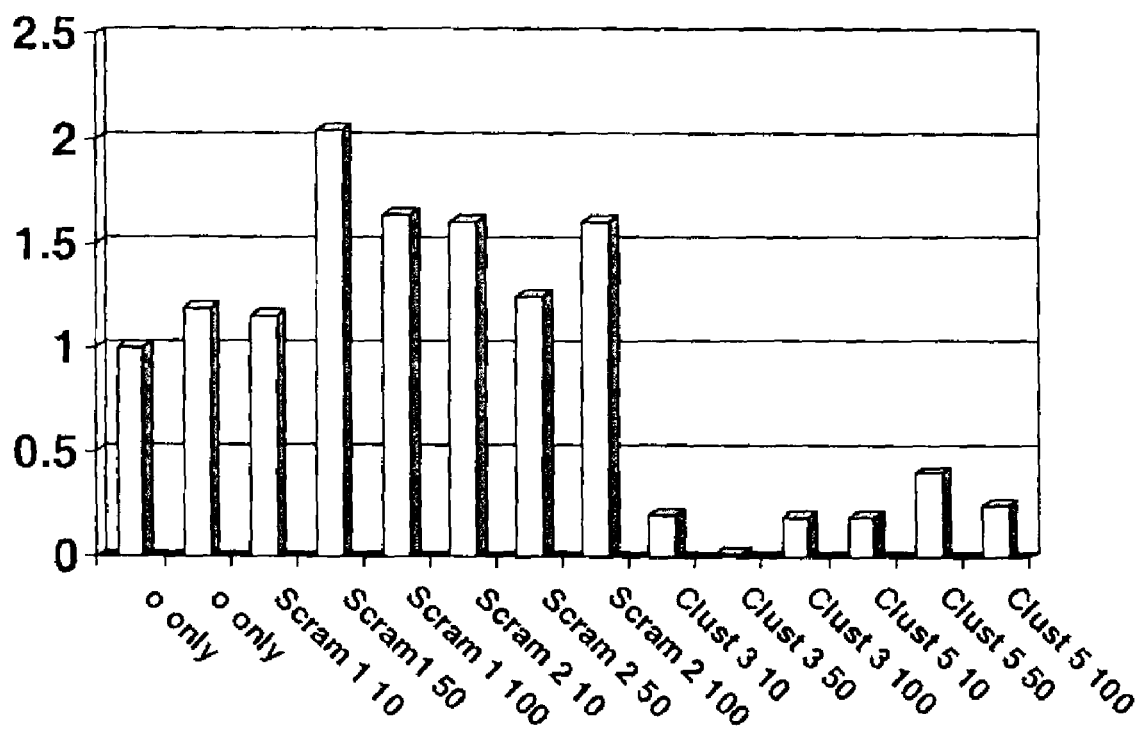
FIG. 10 shows the reduction in clusterin transcript as a result of treatment of P03 cells with clusterin-targeted siRNA as determined by Northern blot.

PC3 cells were treated (1 pulse) with CLU-3 (Seq ID NOs. 5 and 6) or CLU-5 (Seq ID Nos 9 and 10) or with a scrambled control at levels of 10, 50 or 100 nM, or with oligo-FECTAMINE™ only. After two days total RNA was extracted and analyzed for clusterin and GADPH by Northern blotting. Densitometric measurement was performed. FIG. 10 presents results of these measurements after normalization to GADPH. Reduction in the amount of clusterin transcript was observed at all doses of CLU-3 and CLU-5.

EXAMPLE 12

Figure 11:
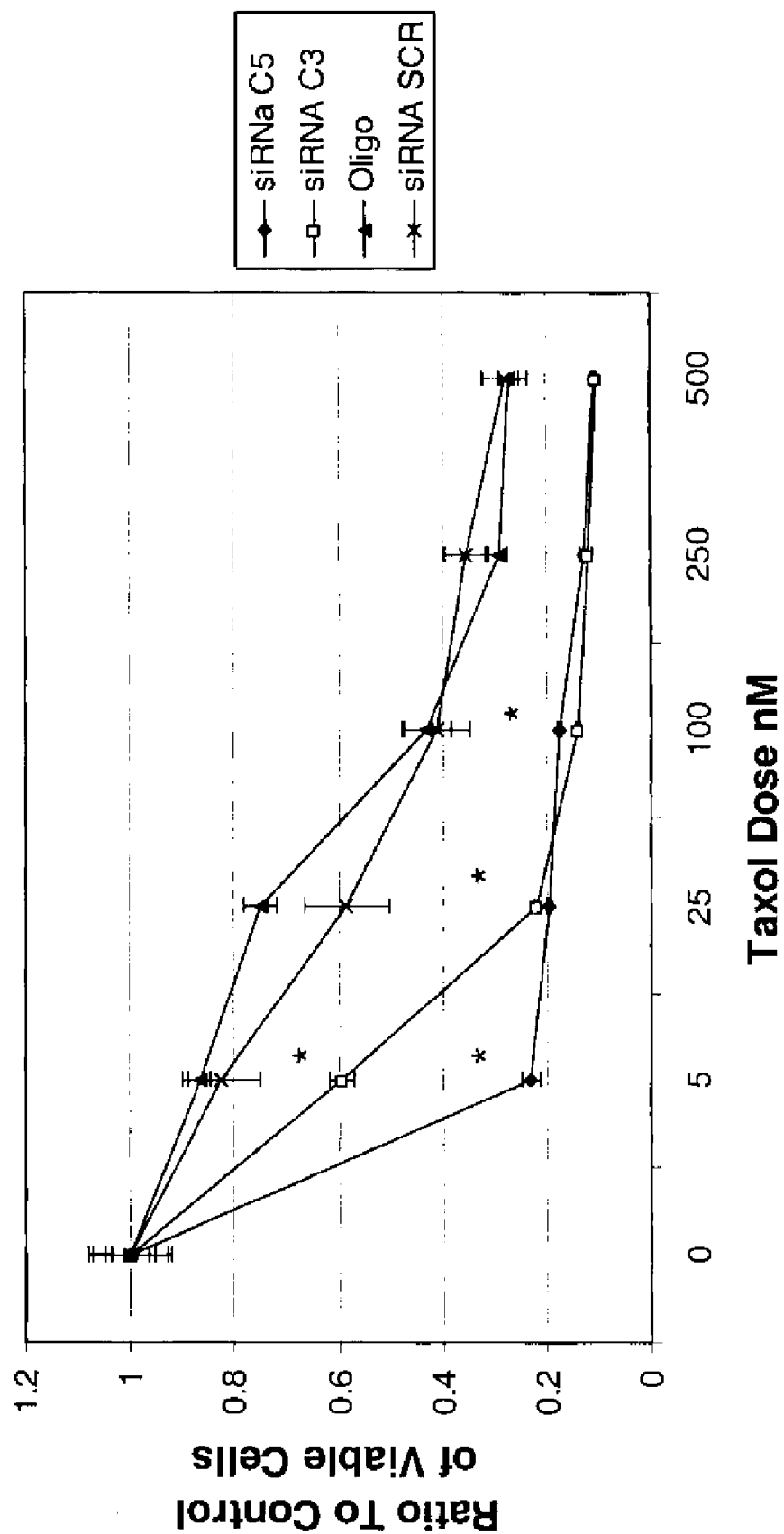
FIG. 11 shows cell viability following treatment of PC3 cells with combinations of siRNA and Taxol.

PC3 cells were treated once with 25 nM human clusterin siRNAs (CLU-3 and CLU-5), a scrambled control, or oligo-FECTAMINE™ only. After two days of treatment, the medium was replaced with medium containing various concentrations of Taxol (Paclitaxel). After three days of incubation, cell viability was determined by MTT assay. FIG. 11 summarizes the results. As can be seen, the siRNA and the Taxol worked in synergy to reduce the number of viable cells.

EXAMPLE 13

Figure 12:
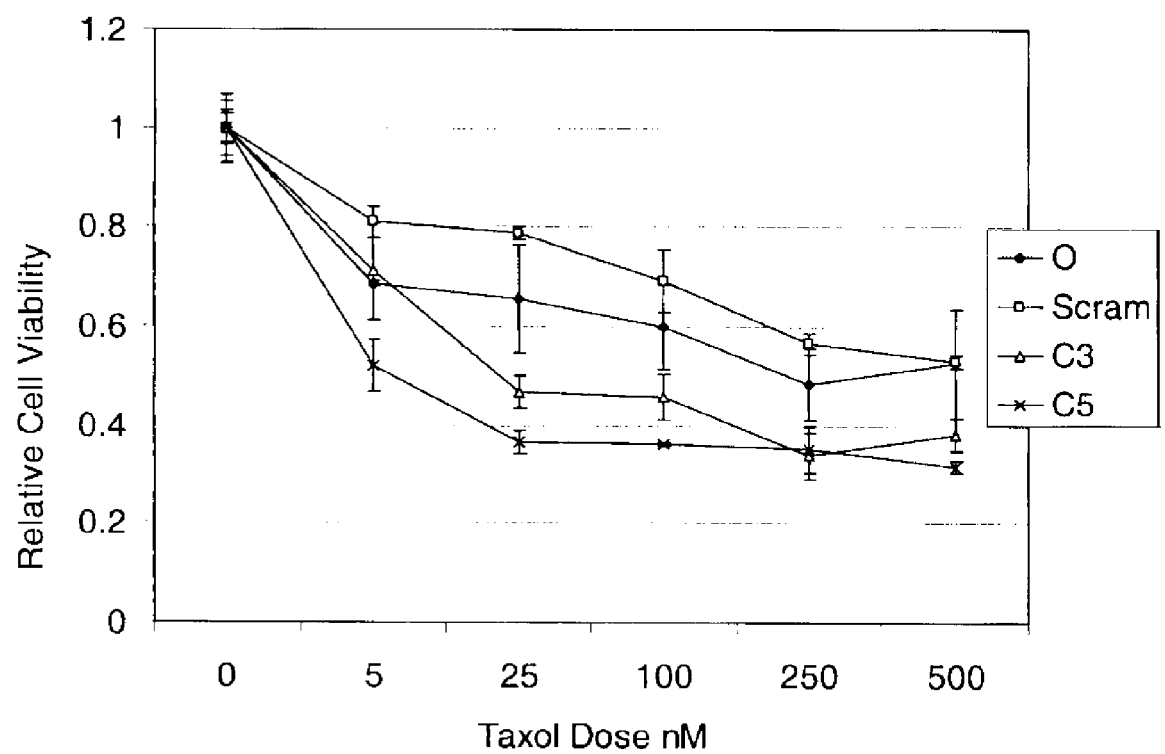
FIG. 12 shows cell viability following treatment of A549 cells with combinations of siRNA and Taxol.

The experiment of Example 12 was repeated with A549 cells in place of PC3 cells. The results are summarized in FIG. 12

EXAMPLE 14

Figure 13:
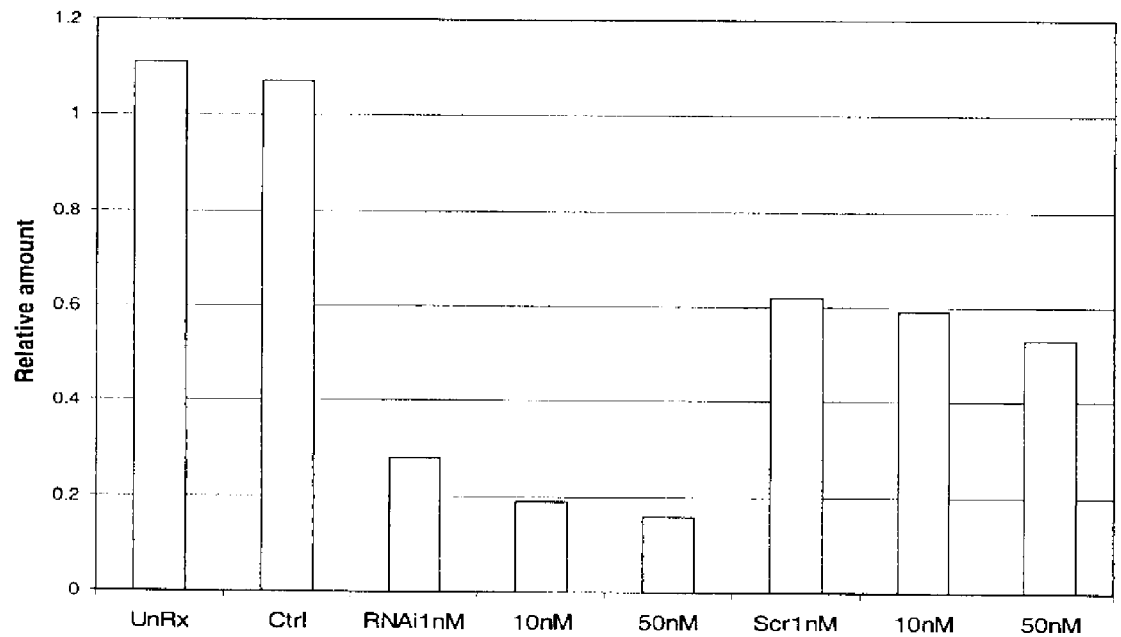
FIG. 13 shows the reduction in clusterin transcript as a result of treatment of OVCAR3 cells with clusterin-targeted siRNA as determined by Northern blot.

OVCAR3 ovarian cancer cells were treated once with 1, 10 or 50 nM CLU5, scrambled control or a vehicle only control. An untreated control was also run. After two days, total RNA was extracted and analyzed for clusterin and GAPDH mRNA by Northern blot. Densitometric measurements of clusterin mRNA levels after normalization to GAPDH mRNA are shown in FIG. 13. Substantial dose dependent reduction in the amount of clusterin transcript was observed.

EXAMPLE 15

Figure 14:
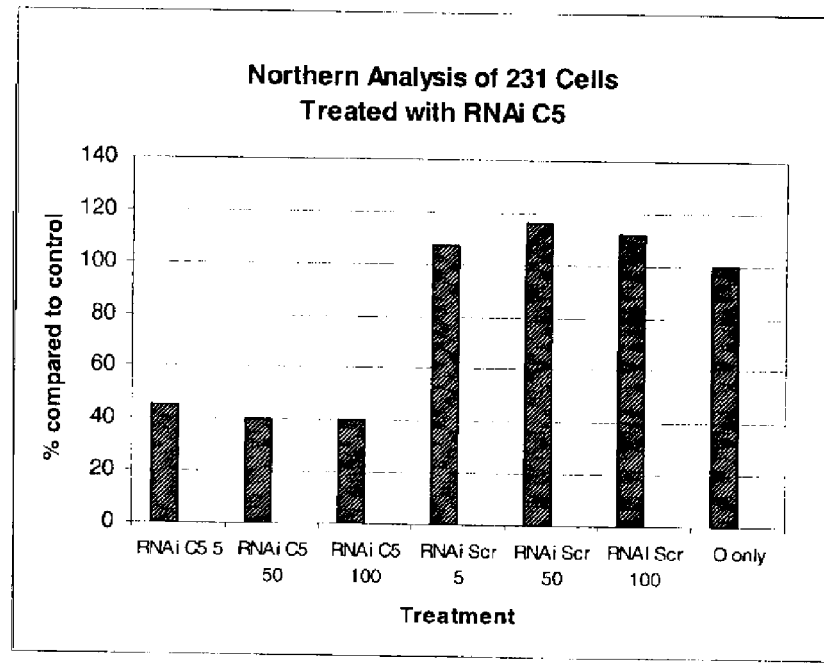
FIG. 14 shows the reduction in clusterin transcript as a result of treatment of MDA-MB 231 cells with clusterin-targeted siRNA as determined by Northern blot.

MDA-MB 231 human breast cancer cells were transfected with 5, 50 or 100 nM CLU-5 or a scrambled control, or with oligoFECTAMINE™ vehicle alone. Two days after transfection, RNA was extracted and analyzed for clusterin and GAPDH by Northern blotting. Densitometric measurements of clusterin mRNA levels after normalization to GAPDH mRNA are shown in FIG. 14. Substantial reduction in the amount of clusterin transcript was observed.

EXAMPLE 16

Figure 15:
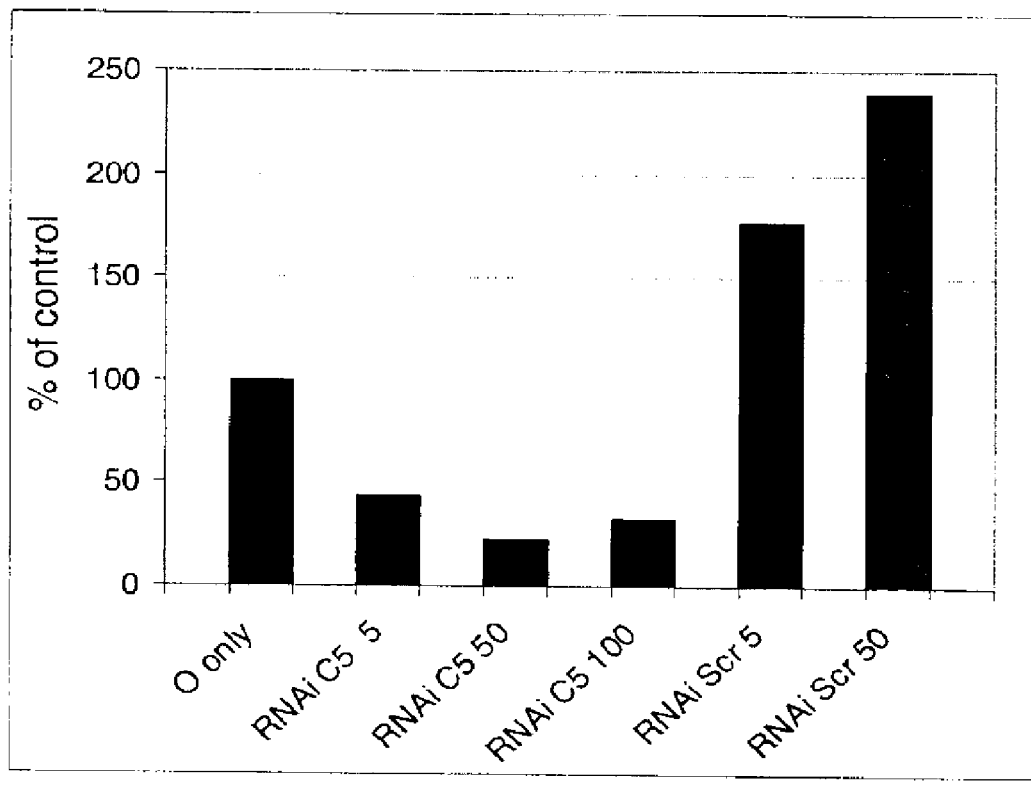
FIG. 15 shows the reduction ill clusterin transcript as a result of treatment of MDA-MB 231 cells with clusterin-targeted siRNA as determined by RT-PCR.

The experiment of Example 15 was repeated, except that clusterin transcript was quantified using RT-PCR. The results are summarized in FIG. 15. Substantial reduction in the amount of clusterin transcript was observed.

EXAMPLE 17

Figure 16:
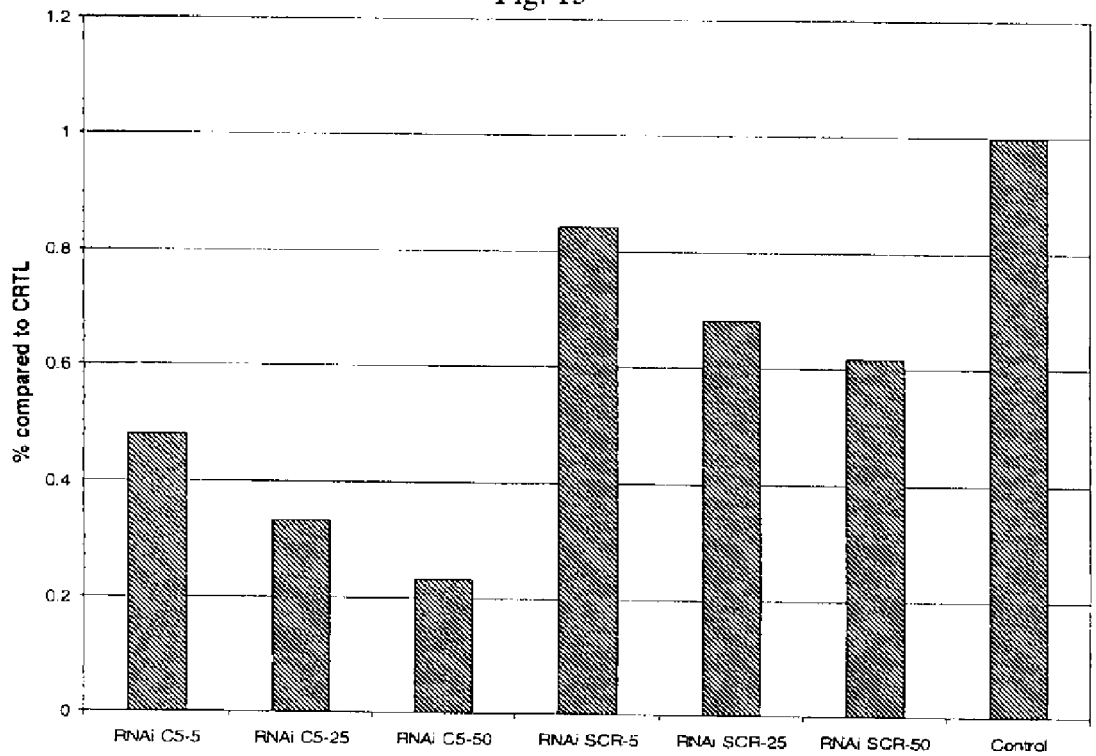
FIG. 16 shows the reduction in clusterin transcript as a result of treatment of MCF-7 cells with clusterin-targeted siRNA as determined by Northern blot.

MCF-7 human breast cancer cells were transfected with 5, 25 or 50 nM CLU-5 or a scrambled control, or with oligo-FECTAMINE™ vehicle alone. Two days after transfection, RNA was extracted and analyzed for clusterin and GAPDH by Northern blotting. Densitometric measurements of clusterin mRNA levels after normalization to GAPDH mRNA are shown in FIG. 16. Substantial dose-dependent reduction in the amount of clusterin transcript was observed.

EXAMPLE 18

Figure 17:
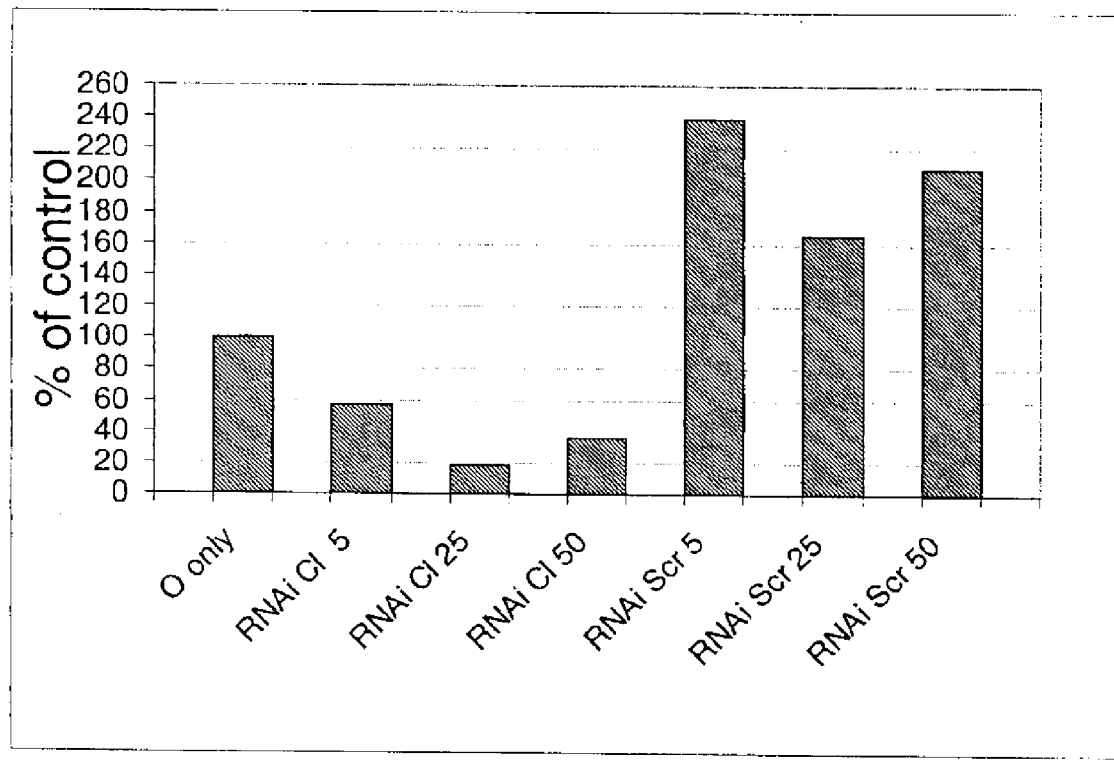
FIG. 17 shows the reduction in clusterin transcript as a result of treatment of MCF-7 cells with clusterin-targeted siRNA as determined by RT-PCR.

The experiment of Example 17 was repeated, except that clusterin transcript was quantified using RT-PCR. The results are summarized in FIG. 17. Substantial reduction in the amount of clusterin transcript was observed.

EXAMPLE 19

Figure 18:
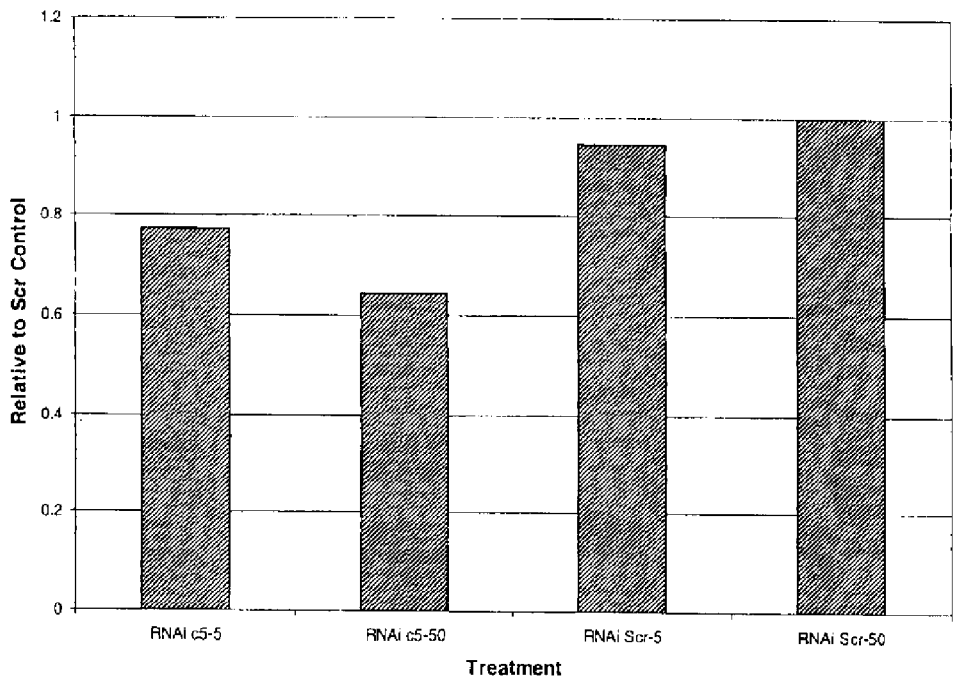
FIG. 18 shows the reduction in the amount of clusterin protein in MCF-7 cells treated with the siRNA relative to the scrambled control.

MCF-7 cells were transfected with various doses (5 and 50 nM) of CLU-5 siRNA or scrambled control. Three days after treatment, proteins were extracted and analyzed by Western blotting for clusterin levels (MW=40 and 60 kDa). FIG. 18 shows the reduction in the amount of clusterin protein in cells treated with the siRNA relative to the scrambled control.

EXAMPLE 20

Clusterin overexpressing LNCaP)/T1 cells were transfected (1 pulse) with 10 nM CLU-5 siRNA or scrambled control. Three days after treatment, the proteins were extracted and analyzed by Western blotting for clusterin. No clusterin was detected in the cells treated with the siRNA.

EXAMPLE 21

Figure 19:
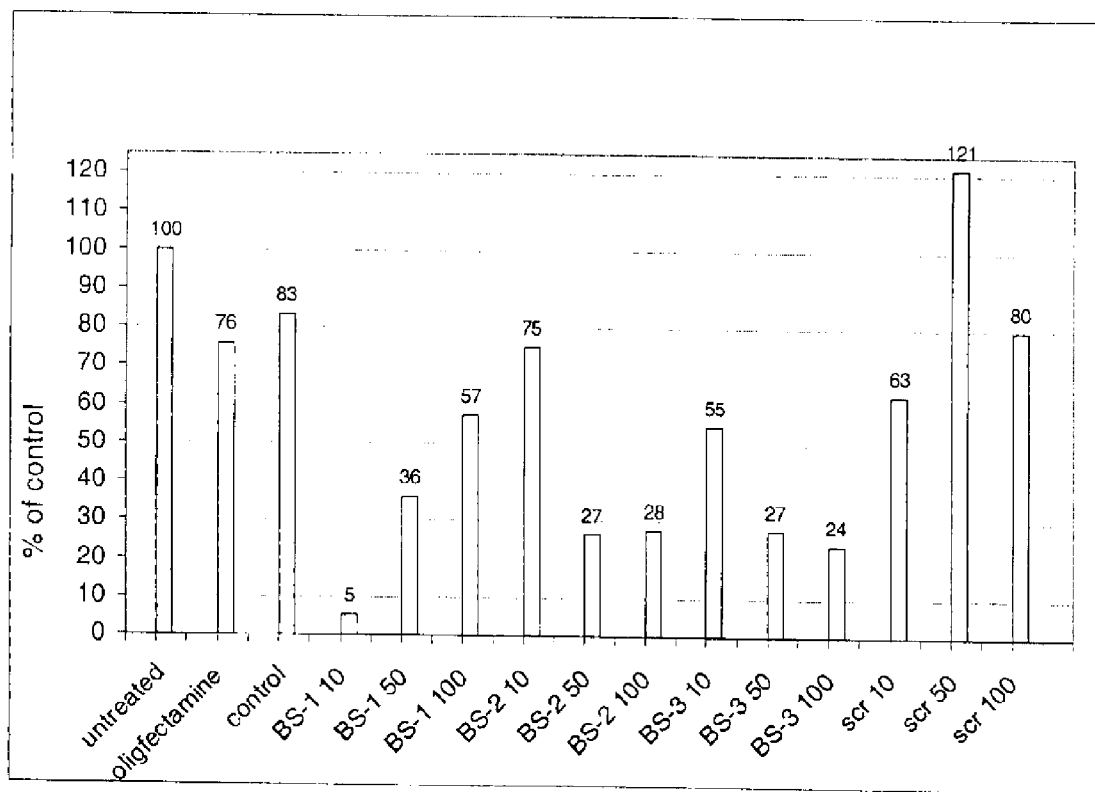
FIG. 19 shows the reduction in IGFBP-2 transcript as a result of treatment of A549 cells with bispecific IGFBP-2 and -5-targeted siRNA as determined by RT-PCR.

3 species of siRNA targeting IGFBP-2 and -5 were formed as double-stranded RNA from Seq. ID NOs. 39 and 40, 41 and 42, and 43 and 44 and labeled as BS-1-BS-3, respectively. A549 cells were transfected with various doses (10, 50 and 100 nM) of the 3 species of siRNA or scrambled control. A vehicle only control and an untreated control were also evaluated. Total RNA was extracted and analyzed by RT-PCR for IGFBP-2 transcript. As shown in FIG. 19, reduction in the amount of IGFBP-2 transcript was observed with all three species of siRNA.

EXAMPLE 22

Figure 20:
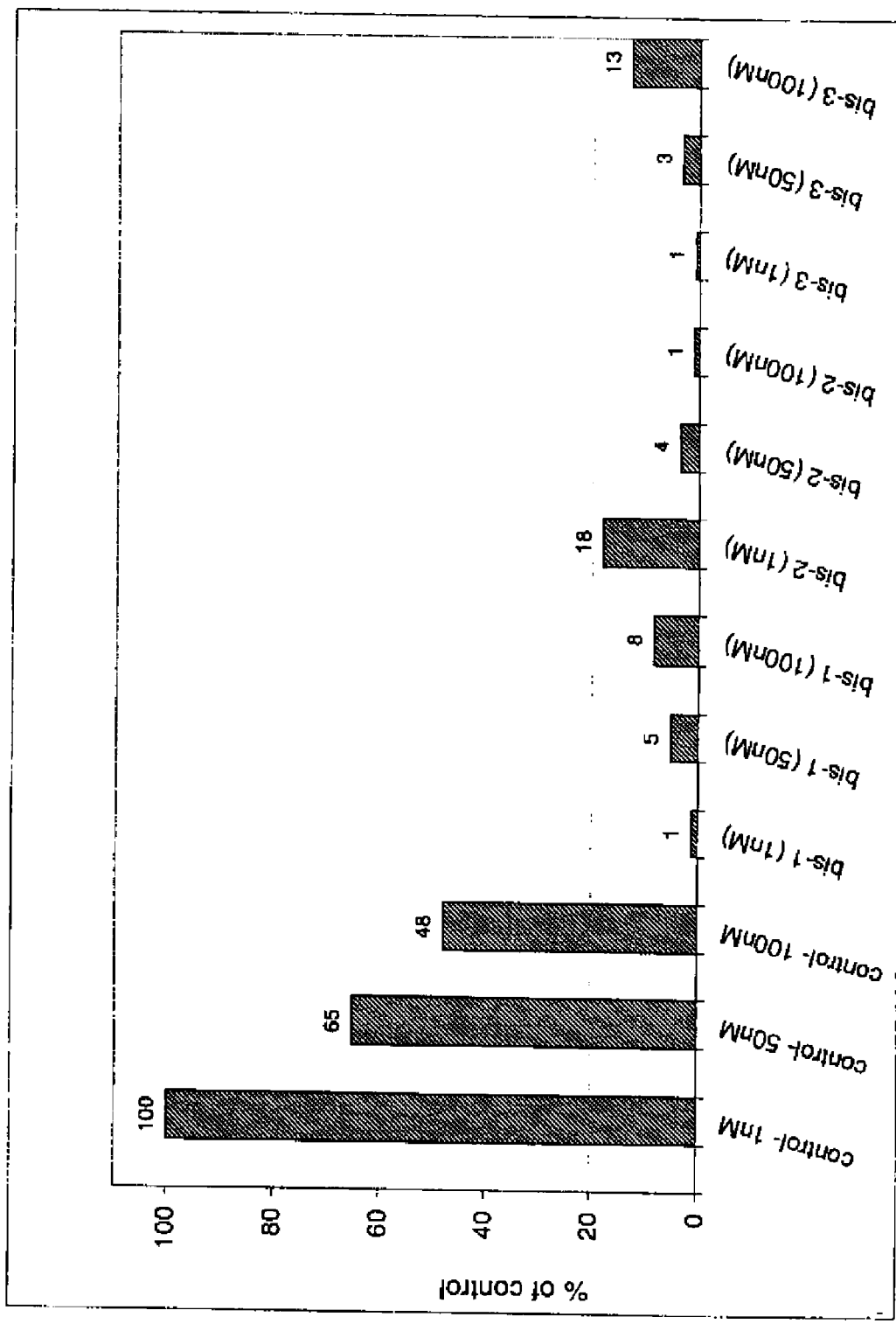
FIG. 20 shows the reduction in IGFBP-5 transcript as a result of treatment of PC3 cells with bispecific IGFBP-2 and -5-targeted siRNA as determined by RT-PCR.
Figure 21:
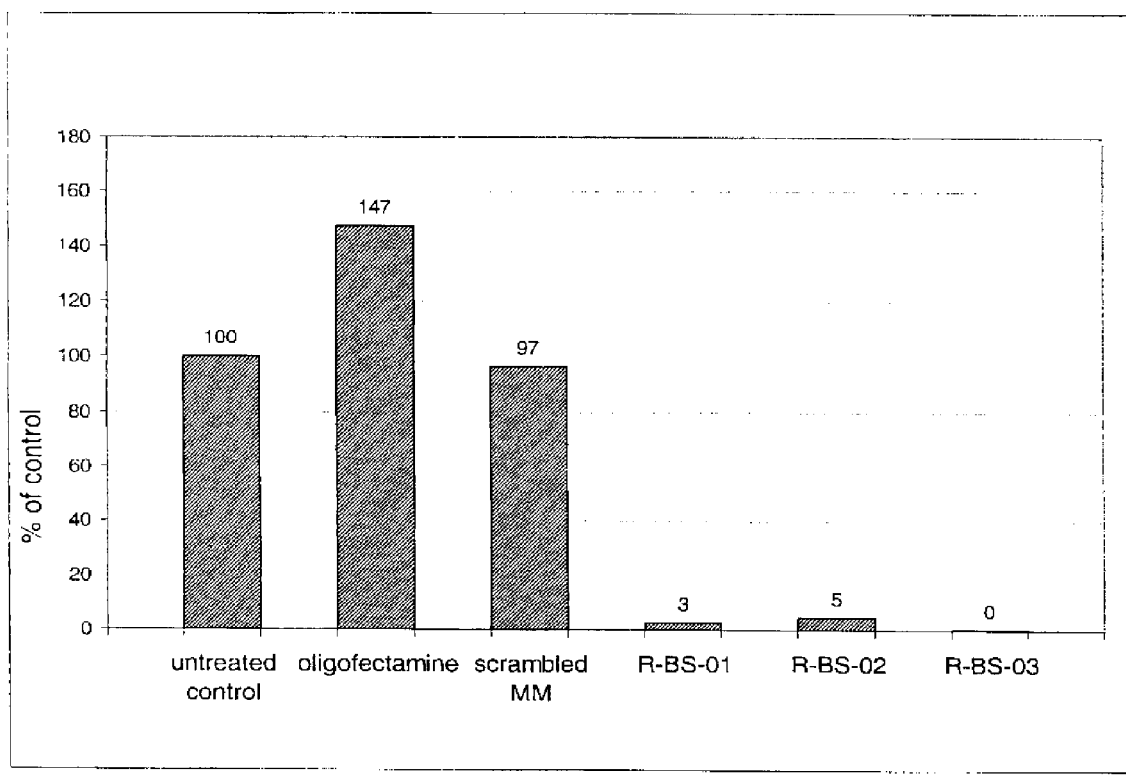
FIG. 21 shows reduction in IGFBP-5 mRNA in PC3 cells.

PC3 cells were transfected with various doses (10, 50 and 100 nM) of the 3 species of bispecies siRNA (BS-1, BS-2 and BS-3) or scrambled control. A vehicle only control was also evaluated. Total RNA was extracted and analyzed by RT-PCR for IGFBP-5 transcript. As shown in FIGS. 20 and 21, reduction in the amount of IGFBP-5 transcript was observed with all three species of siRNA.

EXAMPLE 23

Figure 22:
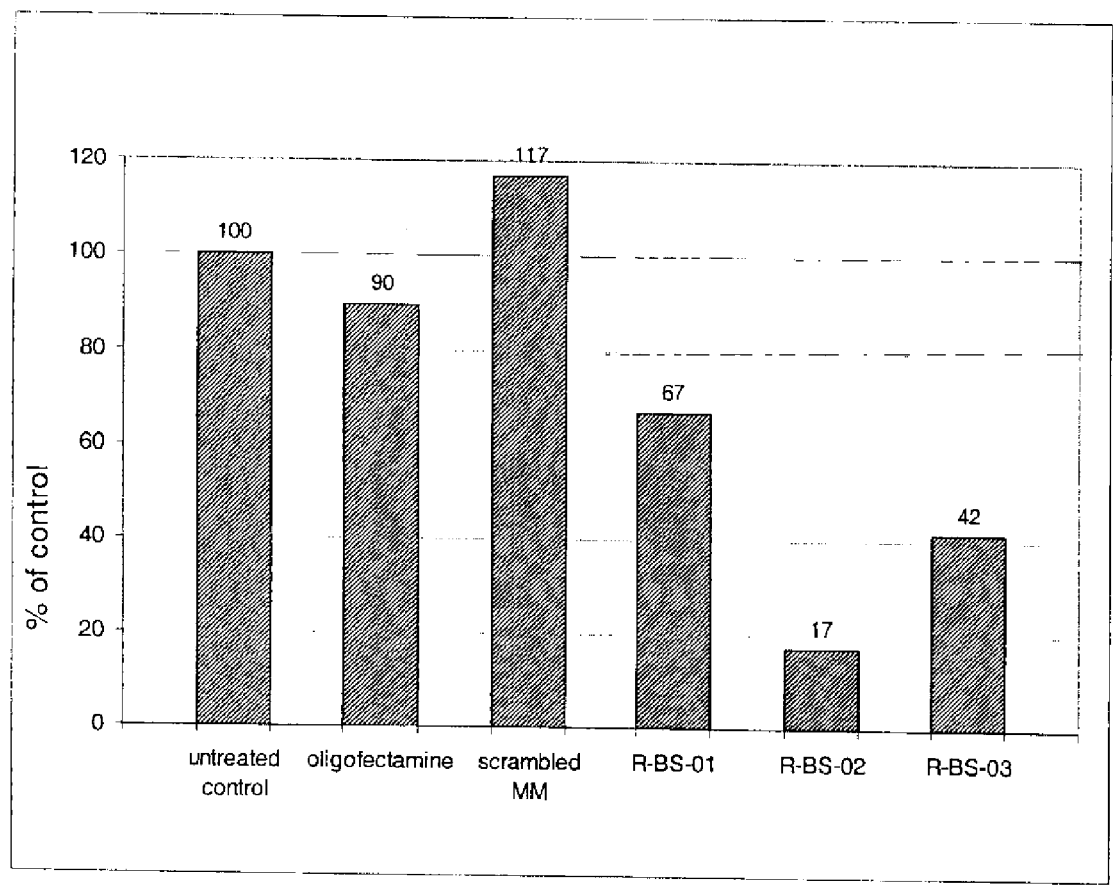
FIG. 22 shows inhibitions of IGFBP-5 transcript in primary human bone fibroblast.

Primary human bone fibroblasts were transfected with 50 nM of the 3 species of bispecific siRNA (BS-1, BS-2 and BS-3) or scrambled control. A vehicle only and an untreated control were was also evaluated. Total RNA was extracted and analyzed by RT-PCR for IGFBP-5 transcript. As shown in FIGS. 22, reduction in the amount of IGFBP-5 transcript was observed with all three species of siRNA.

EXAMPLE 24

Figure 23:
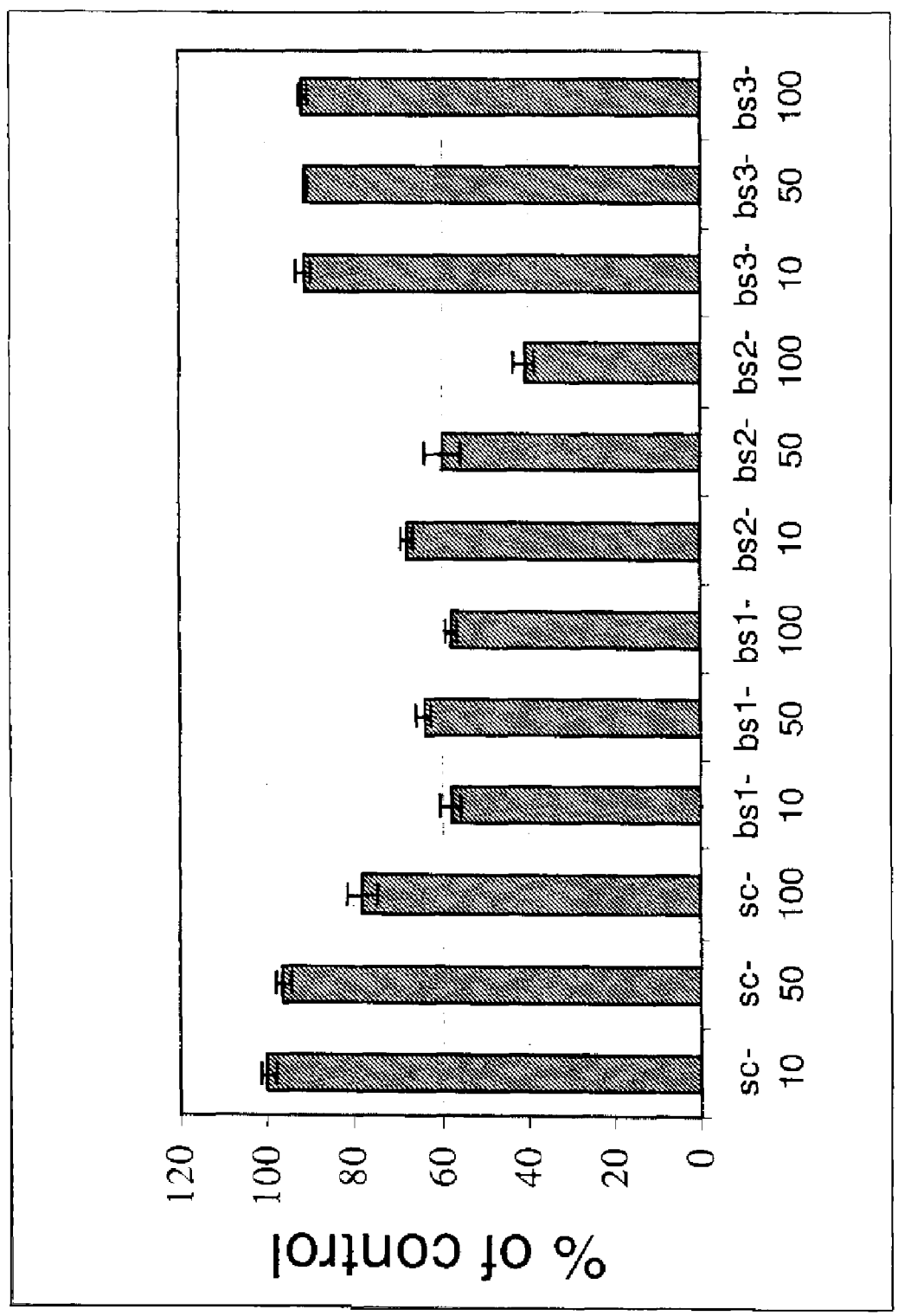
FIG. 23 shows growth inhibition of C42 cells by IGFBP-2/IGFBP-5 bispecific siRNA.

C42 cells (a sub-line of LNCaP prostate cancer cells) were treated with BS-1, BS-2, and BS-3, and growth inhibition was assessed using a crystal violet assay. The results are shown in FIG. 23.

EXAMPLE 25

Figure 24:
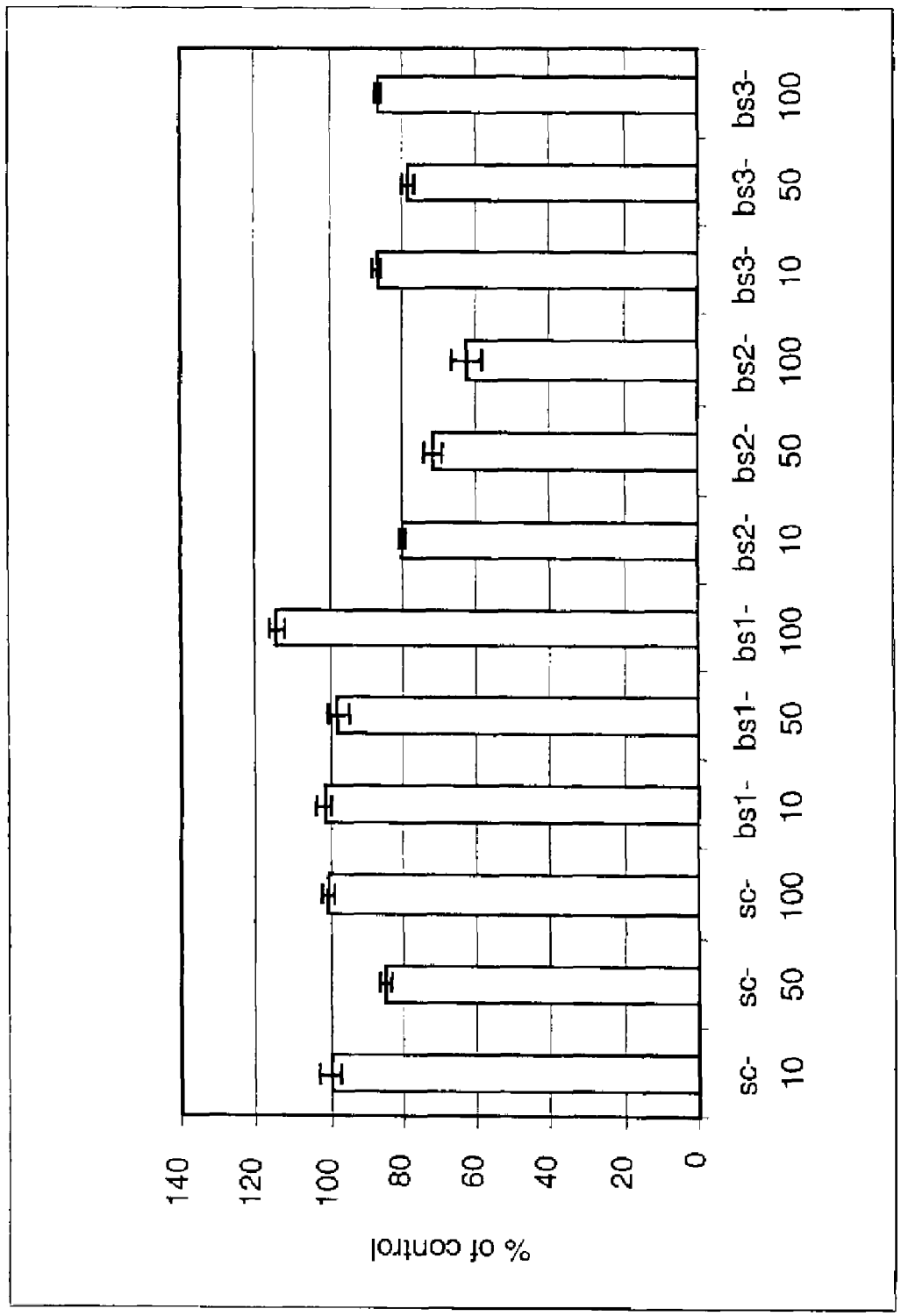
FIG. 24 shows growth inhibition of A549 cells by IGFBP-2/IGFBP-5 bispecific siRNA.

A549 lung cancer cells were treated with BS-1, BS-2, and BS-3, and growth inhibition was assessed using a crystal violet assay. The results are shown mi FIG. 24.

The invention claimed is:

1. An RNA molecule wherein the RNA is single or double stranded, and wherein substantially all of the RNA molecule is complementary to the sense or antisense strand of a gene encoding human IGFBP-2 and substantially all of the RNA molecule is also complementary to a gene encoding human IGFBP-5, and wherein the RNA molecule when in double stranded form is effective mediate degradation or block translation of mRNA that is the transcriptional product of both human IGFBP-2 and human IGFBP-5 through an RNAi mechanism.

2. The RNA molecule of claim 1, wherein the molecule has a length of 16 to 29 nucleotides.

3. The RNA molecule of claim 2, wherein the molecule has a length of 18 to 23 nucleotides.

4. The RNAi molecule of claim 3, wherein the RNA molecule consists of a sequence selected from among Seq ID Nos 39 to 44 or a double stranded molecule containing a single strand selected from Seq ID Nos 39 to 44.

5. A composition comprising an RNA molecule, wherein the RNA molecule is single or double stranded, and wherein substantially all of the RNA molecule is complementary to the sense or antisense strand of a gene encoding human IGFBP-2 and substantially all of the RNA molecule is also complementary to a gene encoding human IGFBP-5, and wherein the RNA molecule when in double-stranded form is effective to mediate degradation or block translation of mRNA that is the transcriptional product of both human IGFBP-2 and human IGFBP-5 through an RNAi mechanism, together with a pharmaceutically acceptable carrier.

6. The composition of claim 5, wherein the pharmaceutically acceptable carrier is a sterile injectable solution.

7. The composition of claim 6, wherein the molecule has a length of 16 to 29 nucleotides.

8. The composition of claim 7, wherein the molecule has a length of 18 to 23 nucleotides.

9. The composition of claim 8, wherein the RNA molecule wherein molecule consists of a sequence selected from among Seq ID Nos 39 to 44 or a double stranded molecule containing a single strand selected from Seq ID Nos 39 to 44.

10. The RNA molecule of claim 3, wherein the RNA molecule consists of Seq ID No 41 or 42 or a double stranded molecule consisting of Seq ID Nos 41 and 42.

11. The RNA molecule of claim 3, wherein the RNA molecule comprises Seq ID No 41 or 42 or a double stranded molecule comprising Seq ID Nos 41 and 42.

12. The composition of claim 8, wherein the RNA molecule consists of Seq ID No 41 or 42 or a double stranded molecule consisting of Seq ID Nos 41 and 42.

13. The composition of claim 8, wherein the RNA molecule comprises Seq ID No 41 or 42 or a double stranded molecule comprising Seq ID Nos 41 and 42.

14. The RNA molecule of claim 1, wherein the RNA molecule is double stranded.

15. The RNA molecule of claim 4, wherein the RNA molecule is double stranded.

16. The composition of claim 5, wherein the RNA molecule is double stranded.

17. The composition of claim 9, wherein the RNA molecule is double stranded.

18. The RNA molecule of claim 10, wherein the RNA molecule is double stranded.

19. The RNA molecule of claim 11, wherein the RNA molecule is double stranded.

20. The composition of claim 12, wherein the RNA molecule is double stranded.

21. The composition of claim 13, wherein the RNA molecule is double stranded.

* * * * *

UNITED STATES PATENT AND TRADEMARK OFFICE
CERTIFICATE OF CORRECTION

| | | |
|---|---|---|
| PATENT NO. | : 7,964,717 B2 | Page 1 of 1 |
| APPLICATION NO. | : 11/276300 | |
| DATED | : June 21, 2011 | |
| INVENTOR(S) | : Gleave et al. | |

It is certified that error appears in the above-identified patent and that said Letters Patent is hereby corrected as shown below:

Column 39, Claim 1, Lines 20 through 22 should read: -- IGFBP-5, and wherein the RNA molecule when in double stranded form is effective to mediate degradation or block translation of mRNA that is the transcriptional product of both --

Column 40, Claim 9, Lines 15 and 16 should read: -- The composition of claim 8, wherein the RNA molecule consists of a sequence selected from --

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

PATENT NO.         : 7,964,717 B2                                         Page 1 of 1
APPLICATION NO.    : 11/276300
DATED              : May 20, 2014
INVENTOR(S)        : Gleave et al.

It is certified that error appears in the above-identified patent and that said Letters Patent is hereby corrected as shown below:

In the Claims

In Column 39, Lines 29-32, Claim 4 should read: -- The RNA molecule of claim 3, wherein the RNA molecule consists of a sequence selected from among Seq ID Nos 39 to 44 or a double stranded molecule containing a single strand selected from Seq ID Nos 39 to 44. --

Signed and Sealed this
Second Day of September, 2014

Michelle K. Lee
*Deputy Director of the United States Patent and Trademark Office*